(12) United States Patent
Rothbard et al.

(10) Patent No.: US 6,495,663 B1
(45) Date of Patent: Dec. 17, 2002

(54) METHOD AND COMPOSITION FOR ENHANCING TRANSPORT ACROSS BIOLOGICAL MEMBRANES

(75) Inventors: Jonathan B. Rothbard, Woodside, CA (US); Paul A. Wender, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/396,195

(22) Filed: Sep. 14, 1999

Related U.S. Application Data

(63) Continuation of application No. 09/083,259, filed on May 21, 1998, now Pat. No. 6,306,993.
(60) Provisional application No. 60/047,345, filed on May 21, 1997, now abandoned.

(51) Int. Cl.⁷ .................................................. C07K 7/00
(52) U.S. Cl. ...................... 530/329; 530/324; 530/325; 530/326; 530/327; 530/328; 514/12; 514/13; 514/14; 514/15; 514/16; 514/17
(58) Field of Search ................................ 514/2, 12–17; 530/324–329

(56) References Cited

U.S. PATENT DOCUMENTS

| | | | | |
|---|---|---|---|---|
| 3,915,800 A | * | 10/1975 | Kang ........................ 195/31 P |
| 4,053,638 A | * | 10/1977 | Litchfield .................... 424/33 |
| 4,083,974 A | * | 4/1978 | Turi ............................ 424/241 |
| 4,532,207 A | | 7/1985 | Brewer et al. ................. 435/68 |
| 4,631,190 A | | 12/1986 | Shen et al. .................... 424/85 |
| 4,701,521 A | | 10/1987 | Ryser et al. .................. 530/322 |
| 4,847,240 A | | 7/1989 | Ryser et al. .................. 514/12 |
| 4,880,911 A | | 11/1989 | Brewer et al. ............... 530/351 |
| 4,883,661 A | * | 11/1989 | Daly ........................ 424/85.2 |
| 5,162,505 A | | 11/1992 | Dean et al. ............... 530/391.5 |
| 5,241,078 A | * | 8/1993 | Moreland .................... 548/542 |
| 5,354,844 A | | 10/1994 | Beug et al. .................. 530/345 |
| 5,387,578 A | * | 2/1995 | Angelucci .................... 514/21 |
| 5,434,257 A | * | 7/1995 | Matteucci ................. 536/24.3 |
| 5,576,351 A | * | 11/1996 | Yoshimura .................. 514/565 |
| 5,633,230 A | | 5/1997 | Twist et al. .................... 514/15 |
| 5,646,120 A | | 7/1997 | Sumner-Smith et al. ...... 514/14 |
| 5,674,849 A | | 10/1997 | Twist et al. .................... 514/15 |
| 5,716,614 A | | 2/1998 | Katz et al. ................. 424/34.3 |
| 5,783,178 A | | 7/1998 | Kabanov et al. .......... 424/78.31 |
| 5,789,531 A | | 8/1998 | Sumner-Smith et al. .... 530/328 |
| 5,795,909 A | | 8/1998 | Shashoua .................... 514/449 |
| 5,831,001 A | | 11/1998 | Twist et al. ................. 530/328 |
| 5,918,568 A | * | 7/1999 | Gjerlov ........................ 119/650 |
| 6,110,908 A | * | 8/2000 | Guthery ...................... 514/188 |

FOREIGN PATENT DOCUMENTS

| | | |
|---|---|---|
| CA | 2094658 | 10/1993 |
| EP | 0 009 498 | 6/1984 |
| EP | 0 599 303 | 6/1994 |
| EP | 0599303 | 6/1994 |
| WO | 79/00515 | 8/1979 |
| WO | WO 79/00515 | 8/1979 |
| WO | WO 91/09958 | 7/1991 |
| WO | 91/09958 | 7/1991 |
| WO | 92/07871 | 5/1992 |
| WO | WO 92/07871 | 5/1992 |
| WO | WO 93/04701 | 3/1993 |
| WO | 93/04701 | 3/1993 |
| WO | WO 93/21941 | 11/1993 |
| WO | 93/21941 | 11/1993 |
| WO | WO 94/04686 | 3/1994 |
| WO | 94/04686 | 3/1994 |
| WO | 94/14464 | 7/1994 |
| WO | WO 94/14464 | 7/1994 |
| WO | WO 95/11038 | 4/1995 |
| WO | 95/11038 | 4/1995 |
| WO | 96/21036 | 7/1996 |
| WO | WO 96/21036 | 7/1996 |
| WO | 97/33552 | 9/1997 |
| WO | WO 97/33552 | 9/1997 |
| WO | WO 97/40854 | 11/1997 |
| WO | 97/40854 | 11/1997 |

OTHER PUBLICATIONS

Docherty Antimicrob Agents Chemother 31, 1562, 1987.*
Mauersberger, Exp Pathol (JENA) 13, 268, 1977.*
Devlin, "Textbook of Biochemistry" (Wiley–Liss) pp. 974–975, 1992.*
Sigma Catalog, pp. 1715 & 1721, 1991.*
International Search Report of related PCT application No. US98/10571.
Arbuck, S.G., and Blaylock, B.A., "Taxol: Clinical Results and Current Issues in Development", Chapter 14 in *Taxol: Science and Applications*, Suffness, M., Ed., CRC Press, New York NY, pp. 379–415 (1995).
Balicki, D., et al., "Histone H2A Significantly Enhances In Vitro DNA Transfection," *Molec. Med.* 3:782–787 (1997).
Boussif, O., et al., "A versatile vector for gene and oligonucleotide transfer into cells in culture and in vivo: Polyethylenimine," *Proc. Natl. Acad. Sci.* 92:7297–7301 (1995).

(List continued on next page.)

*Primary Examiner*—Christopher S. F. Low
*Assistant Examiner*—David Lukton
(74) *Attorney, Agent, or Firm*—Reed & Associates

(57) ABSTRACT

Methods and compositions for transporting drugs and macromolecules across biological membranes are disclosed. In one embodiment, the invention includes a method for enhancing transport of a selected compound across a biological membrane, wherein a biological membrane is contacted with a conjugate containing a biologically active agent that is covalently attached to a transport polymer. In one embodiment, the polymer consists of from 6 to 25 subunits, at least 50% of which contain a guanidino or amidino sidechain moiety. The polymer is effective to impart to the attached agent a rate of trans-membrane transport across a biological membrane that is greater than the rate of trans-membrane transport of the agent in non-conjugated form.

18 Claims, 8 Drawing Sheets

OTHER PUBLICATIONS

Brugidou, J., et al., "The Retro–Inverso Form of A Homeobox–Derived Short Peptide in Rapidly Internalised by Cultured Neurones: A New Basis For An Efficient Intracellular Delivery System," *Biochem. Biophys. Res. Comm.* 214:685–693 (1995).

Burton, K.A., et al., "Basic polyelectrolytes and protein transport across the newborn pig intestine," *J. Physiol.* 211(2):27P–28P (1970).

Buschle, M. et al., "Transloading of tumor antigen–derived peptides in antigen–presenting cells," *Proc. Natl. Acad. Sci.* 94:3256–3261 (1997).

Chen, J., et al., "Galactosylated Histone–Mediated Gene Transfer and Expression," *Human Gene Ther.* 5:429–435 (1994).

Derossi, D., et al., "The Third Helix of the Antennapedia Homeodomain Translocates through Biological Membranes," *J. Biol. Chem.* 269:10444–10450 (1994).

Elferink, J.G.R., "Changes of Plasma Membranes Permeability in Neutrophils Treated with Polycations," *Inflammation* 15(2):103–115 1991.

Emi, N., et al., "Gene Transfer Mediated by Polyarginine Requires a Formation of Big Carrier–Complex of DNA Aggregate," *Biochem. Biophys. Res. Comm.* 231:421–424 (1997).

Fawell, S., et al., "Tat–mediated delivery of heterologous proteins into cells," *Proc. Natl. Acad. Sci.* 91:664–668 (1994).

Fletcher, M.D., and Campbell, M.M., "Partially Modified Retro–Inverso Peptides: Development, Synthesis and Conformational Behavior," *Chem. Rev.* 98:763–795 (1998).

Georg., G.I., "The Medicinal Chemistry of Taxol", Chapter 13 in *Taxol: Science and Applications*, Suffness, M., Ed., CRC Press, New York NY, pp. 317–375 (1995).

Kessler, H., "Peptoids–A New Approach to the Development of Pharmaceuticals," *Angew. Chem. Int. Ed. Engl.* 32:543–544 (1993).

Kingston, D.G:I., "Natural Taxoids: Structure and Chemistry", Chapter 12 in *Taxol: Science and Applications*, Suffness, M., Ed., CRC Press, New York NY, pp. 287–315 (1995).

Lam, K.S., "The "One–Bead–One–Compound" Combinatorial Library Method," *Chem. Rev.* 97:411–448 (1997).

Mauersberger, B., et al., "Studies on the cytotoxicity of poly–L–arginine, poly–L–lysine and DEAE–dextran in L–cells and mouse embryonic fibroblasts," *Exp Pathol (JENA)* 13(4–5):268–273 1977.

Murphy, J., et al., "A combinatorial approach to the discovery of efficient cationic peptoid reagent for gene delivery," *Proc. Natl. Acad. Sci.* 95:1517–1522 (1998).

Natsume,H., et al., "Screening of Absorption Enhancers for Nasal Peptide and Protein Delivery," 23rd Proc. Int. Symp. Controlled Release Bioact. Mater., Jul. 7–10, 1996, pp. 481–482.

Rose, W.C., "Preclinical Antitumor Activity of Taxanes", Chapter 8 in *Taxol: Science and Applications*, Suffness, M., Ed., CRC Press, New York NY, pp. 209–235 (1995).

Simon et al., "Peptoids: A modular approach to drug discovery," *Proc. Natl. Acad. Sci.* 89:9367;9371 (1992).

Straubinger, R.M., "Biopharmaceutics of Paclitaxel (Taxol): Formulation, Activity, and Pharmacokinetics", Chapter 9 in *Taxol: Science and Applications*, Suffness, M., Ed., CRC Press, New York NY, pp. 237–258 (1995).

Sumner–Smith,M., et al., "Antiherpetic activities of N–α–acetyl–non–D–arginine amide acetate," Chem. Abs. vol. 123, No. 7, Abs. No. 79357, 1995.

Thompson, L.A., and Ellman, J.A., "Synthesis and Applications of Small Molecule Libraries," *Chem. Rev.* 96:555–600 (1996).

Uchida, D., et al., "Polycations Decrease the Transepithelial Resistance of Cultured Tracheal Epithelial Cells," Chest 101(3)(suppl.):33S 1992.

Vyas, D.M., et al., "Phosphatase–Activated Prodrugs of Paclitaxel", Chapter 9 in *Taxane Anticancer Agents*, American Chemical Society, Wachington D.C., (1995).

Zuckermann, R.M., et al., "Efficient Method for the Preparation of Peptoids [Oligo(N–substituted glycines)] by Submonomer Solid–Phase Synthesis," *Chem. Soc.* 114:80–83 (1993).

Arbuck et al. (1995), "Taxol: Clinical Results and Current Issues in Development," *Taxol: Science and Applications*, Suffness, M., Ed., CRC Press, New York, NY, Chapter 14, pp. 379–415.

Balicki et al. (1997), "Histone H2A Significantly Enhances In Vitro DNA Transfection," *Molecular Medicine* 3(11):782–787.

Boussif et al. (1995), "A Versatile Vector for Gene and Oligonucleotide Transfer into Cells in Culture and In Vivo: Polyethylenimine," *Proc. Natl. Acad. Sci.* 92:7297–7301.

Brugidou et al. (1995), "The Retro–Inverso Form of A Homeobox–Derived Short Peptide in Rapidly Internalised by Cultured Neurones: A New Basis for an Efficient Intracellular Delivery System," *Biochemical and Biophysical Research Communications* 214(2):685–693.

Burton et al. (1970), "Basic Polyelectrolytes and Protein Transport Across the Newborn Pig Intestine," *J. Physiol.* 211(2):27P–28P.

Chen et al. (1994), "Galactosylated Histone–Mediated Gene Transfer and Expression," *Human Gene Therapy* 5:429–435.

Elferink (1991), "Changes of Plasma Membranes Permeability in Neutrophils Treated with Polycations," *Inflammation* 15(2):103–115.

Fawell et al. (1994), "Tat–Mediated Delivery of Heterologous Proteins into Cells," *Prop. Natl. Acad. Sci.* 91:664–668.

Fletcher et al. (1998), "Partially Modified Retro–Inverso Peptides: Development, Synthesis and Conformational Behavior," *Chem. Rev.* 98:763–795.

Georg et al. (1995), "The Medicinal Chemistry of Taxol," *Science and Applications*, Suffness, M., Ed., CRC Press, New York, NY, Chapter 13, pp. 317–375.

Kessler (1993), "Peptoids—A New Approach to the Development of Pharmaceuticals," *Angew. Chem. Int. Ed. Engl.* 32(4):543–544.

Kingston (1995), "Natural Taxoids: Structure and Chemistry," *Taxol: Science and Applications*, Suffness, M., Ed., CRC Press, New York, NY, Chapter 12, pp. 287–315.

Lam et al. (1997), "The 'One– Bead–One–Compound' Combinatorial Library Method," *Chem. Rev.* 97:411–448.

Murphy et al. (1998), "A Combinatorial Approach to the Discovery of Efficient Cationic Peptoid Reagents for Gene Delivery," *Proc. Natl. Acad. Sci.* 95:1517–1522.

Natsume et al. (1996), "Screening of Absorption Enhancers for Nasal Peptide and Protein Delivery," *23rd Proceed. Intern. Symp. Controlled Release Bioact. Mater.*, pp. 481–482.

Rose (1995), "Preclinical Antitumor Activity of Taxanes," *Taxol: Science and Applications*, Suffness, M., Ed., CRC Press, New York, NY, Chapter 8, pp. 209–235.

Simon et al. (1992), "Peptoids: A Modular Approach to Drug Discovery," *Proc. Natl. Acad. Sci. 89*:9367–9371.

Straubinger (1995), "Biopharmaceutics of Paclitaxel (Taxol): Formulation, Activity, and Pharmacokinetics," *Taxol: Science and Applications*, Suffness, M., Ed., CRC Press, New York, NY, Chapter 9, pp. 237–258.

Sumner–Smith et al. (1995), "Antiherpetic Activities of N–α–Acetyl–Non–D–Arginine Amide Acetate," *Chem. Abs. 123*(7), Abstract No. 79357.

Thompson et al. (1996), "Synthesis and Applications of Small Molecule Libraries," *Chem. Rev. 96*:555–600.

Uchida et al. (1992), "Polycations Decrease the Transepithelial Resistance of Cultured Tracheal Epithelial Cells," *CHEST 101*(3)(suppl.):33S.

Vyas et al. (1995), "Phosphatase–Activated Prodrugs of Paclitaxel," *Taxane Anticancer Agents*, American Chemical Society, Wachington, DC, Series 583, Chapter 9.

Zuckermann et al. (1993), "Efficient Method for the Preparation of Peptoids [Oligo(N–Substituted Glycines)] by Submonomer Solid–Phase Synthesis," *J. Am. Chem. Soc. 114*:10646–10647.

\* cited by examiner

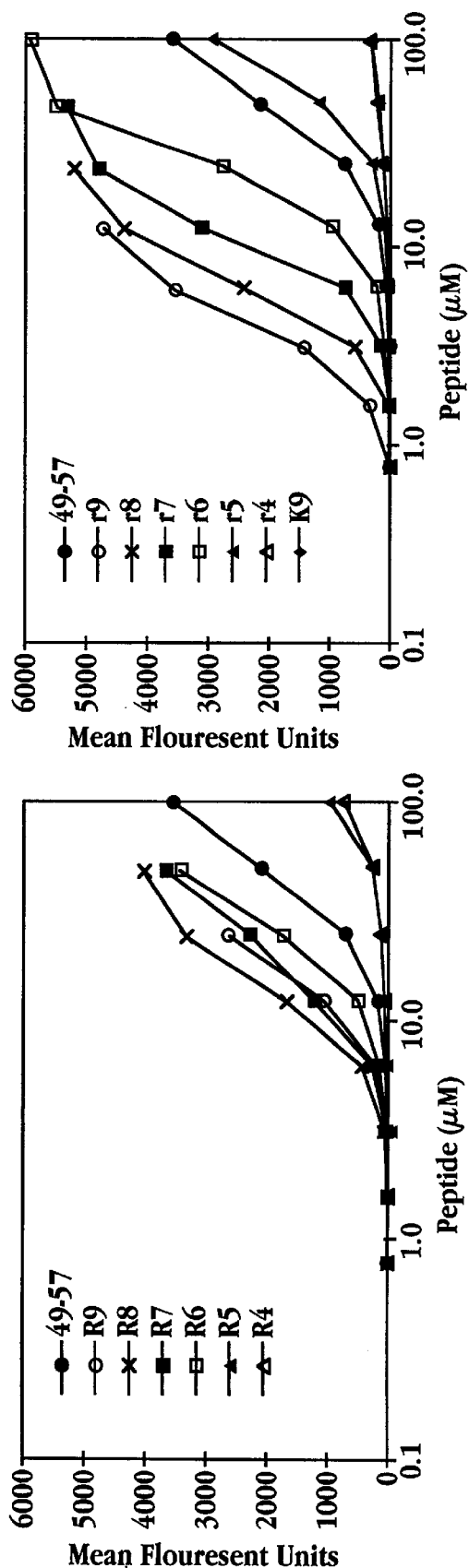
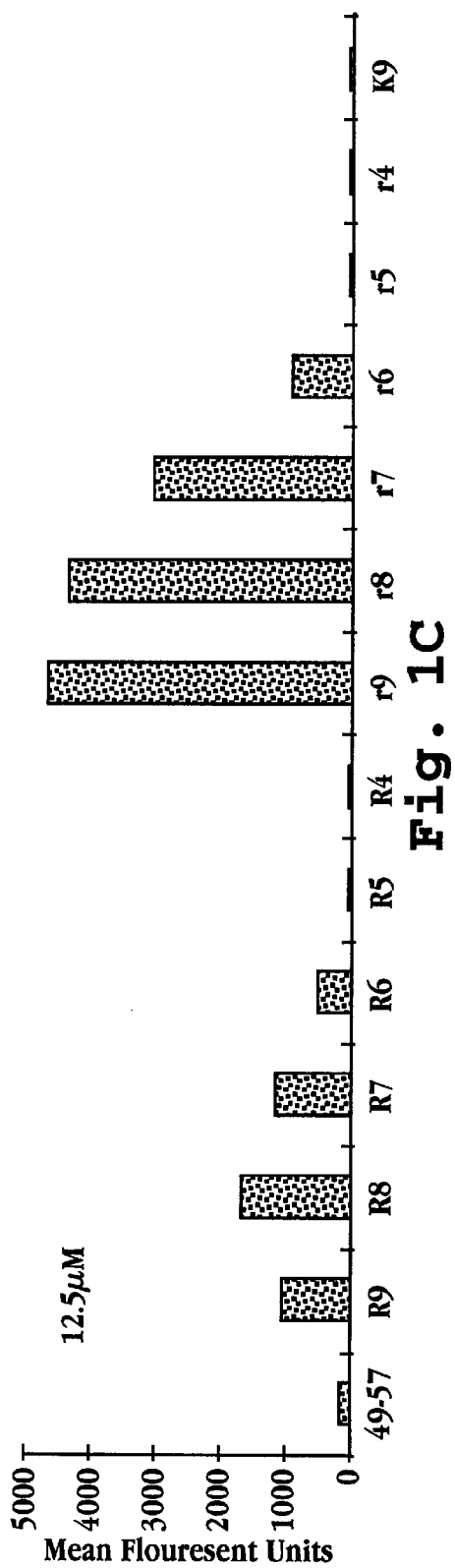
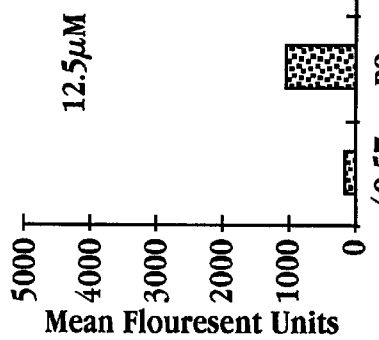
Fig. 1A
Fig. 1B
Fig. 1C

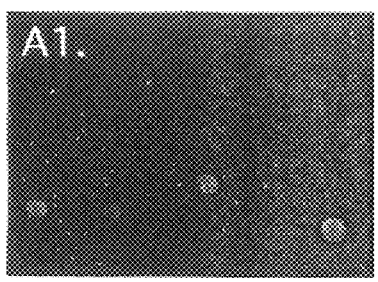
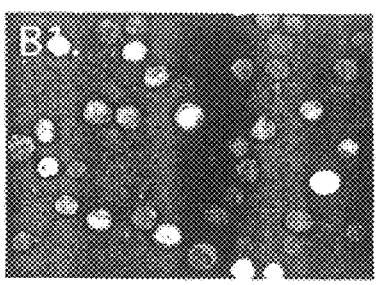
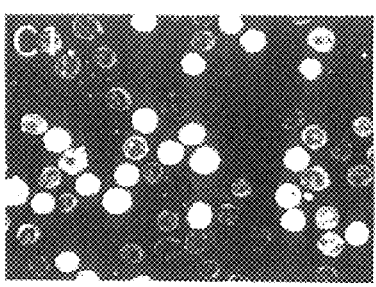
Fig. 2A
Fig. 2B
Fig. 2C
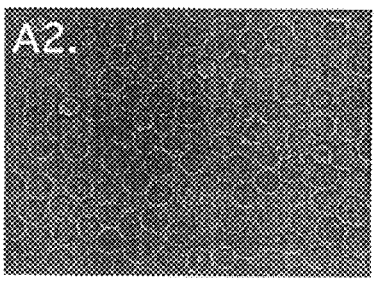
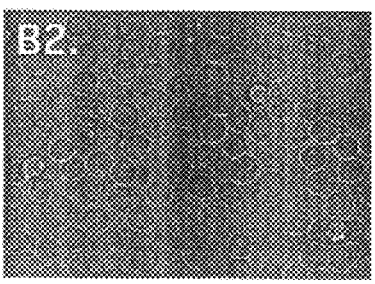
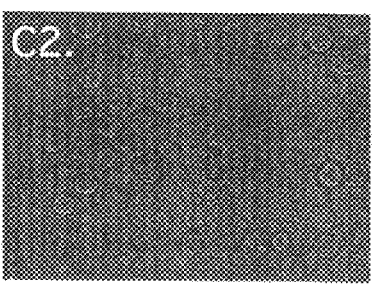
Fig. 2D
Fig. 2E
Fig. 2F

I

II

III

IV

V

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Arg Lys Lys Arg Arg Gln Arg Arg Arg
 1            5

(2) INFORMATION FOR SEQ ID NO:2:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

```
Lys Lys Lys Lys Lys Lys Lys Lys Lys
1               5
```

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Arg Arg Arg Arg
1
```

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Arg Arg Arg Arg Arg
1               5
```

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Arg Arg Arg Arg Arg Arg
1               5
```

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Arg Arg Arg Arg Arg Arg Arg
1               5
```

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide

```
    (xi) SEQUENCE DESCRIPTION: SEQ ID NO:7:

Arg Arg Arg Arg Arg Arg Arg Arg
 1               5

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Arg Arg Arg Arg Arg Arg Arg Arg Arg
 1               5

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Arg Arg Arg Arg Arg Arg Arg Arg Arg Arg Arg Arg Arg Arg Arg
 1               5                  10                  15

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Arg Arg Arg Arg Arg Arg Arg Arg Arg Arg Arg Arg Arg Arg Arg
 1               5                  10                  15

Arg Arg Arg Arg
                20

(2) INFORMATION FOR SEQ ID NO:11:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Arg Arg Arg Arg Arg Arg Arg Arg Arg Arg Arg Arg Arg Arg Arg
 1               5                  10                  15

Arg Arg Arg Arg Arg Arg Arg Arg Arg
                20                  25

(2) INFORMATION FOR SEQ ID NO:12:

(i) SEQUENCE CHARACTERISTICS:
```

(A) LENGTH: 4 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...4
            (D) OTHER INFORMATION: D-Arg (xi) SEQUENCE DESCRIPTION: SEQ ID NO:12:

Arg Arg Arg Arg
 1

(2) INFORMATION FOR SEQ ID NO:13:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...5
            (D) OTHER INFORMATION: D-Arg (xi) SEQUENCE DESCRIPTION: SEQ ID NO:13:

Arg Arg Arg Arg Arg
 1               5

(2) INFORMATION FOR SEQ ID NO:14:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...6
            (D) OTHER INFORMATION: D-Arg (xi) SEQUENCE DESCRIPTION: SEQ ID NO:14:

Arg Arg Arg Arg Arg Arg
 1               5

(2) INFORMATION FOR SEQ ID NO:15:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...7
            (D) OTHER INFORMATION: D-Arg (xi) SEQUENCE DESCRIPTION: SEQ ID NO:15:

Arg Arg Arg Arg Arg Arg Arg
 1               5

```
(2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...8
        (D) OTHER INFORMATION: D-Arg (xi) SEQUENCE DESCRIPTION: SEQ ID NO:16:

Arg Arg Arg Arg Arg Arg Arg Arg
  1               5

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...9
        (D) OTHER INFORMATION: D-Arg (xi) SEQUENCE DESCRIPTION: SEQ ID NO:17:

Arg Arg Arg Arg Arg Arg Arg Arg Arg
  1               5

(2) INFORMATION FOR SEQ ID NO:18:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...10
        (D) OTHER INFORMATION: where the bonds are peptide nucleic
            acid bonds (xi) SEQUENCE DESCRIPTION: SEQ ID NO:18:

AACGCTACAC                                                            10

(2) INFORMATION FOR SEQ ID NO:19:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...10
        (D) OTHER INFORMATION: where the bonds are peptide nucleic
```

-continued

```
        acid bonds (xi) SEQUENCE DESCRIPTION: SEQ ID NO:19:

GTGTAGCGTT                                                                    10

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Cys Ala Ala Ala Arg Arg Arg Arg Arg Arg Arg
1               5                   10

(2) INFORMATION FOR SEQ ID NO:21:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Lys Leu Ser Thr Leu Arg Ser Asn Thr Arg Arg Arg Arg Arg Arg Arg
1               5                   10                  15
```

METHOD AND COMPOSITION FOR ENHANCING TRANSPORT ACROSS BIOLOGICAL MEMBRANES

This application claims priority to application Serial No. 09/083,259 filed May 21, 1998, now U.S. Pat. No. 6,306,993; which claims priority to application Ser. No. 60/047,345 filed on May 21, 1997, now abandoned; which is incorporated herein by reference.

GOVERNMENT INTEREST

This invention was made with the support of NIH grant number CA 65237. Accordingly, the U.S. Government has certain rights in this invention.

FIELD OF THE INVENTION

The present invention is directed to methods and compositions that are effective to enhance transport of biologically active agents, such as organic compounds, polypeptides, oligosaccharides, nucleic acids, and metal ions, across biological membranes.

REFERENCES

Barsoum et al., PCT Pub. No. WO 94/04686 (1994).
Bonifaci, N., et al., *Aids* 9:995–1000.
Brugidou, J., et al. *Biochem. Biophys. Res. Comm.* 214(2): 685–93 (1995).
Derossi, D., et al., *J. Biol. Chem.* 269:10444–50 (1996).
Eghoim, M. O., et al., *Nature* 365:566–568 (1993).
Eberle and Nuninger, *J. Org. Chem.* 57:2689 (1992).
Fawell, S., et al., *Proc. Natl. Acad. Sci. USA* 91:664–668 (1994).
Fletcher, M. D., et al., *Chem. Rev.* 98:763 (1998).
Frankel et al., PCT Pub. No. WO 91/09958 (1991).
Gennaro, A. R., Ed., *REMINGTON'S PHARMACEUTICAL SCIENCES, 18TH ED.*, Mack Publishing Co., Easton, Pa. (1990).
Giannis, A., et al., *Advances Drug Res.* 29:1 (1997).
Kessler, H., *Angew. Chem. Int. Ed. Engl.* 32:543 (1993).
Lam, K. S., et al., *Chem. Rev.* 97:411 (1997).
Langston, S., *DDT* 2:255 (1997).
Rivas, A., et al., *J. Immunol.* 154:4423–33 (1995).
Ruegg, C., et al., *J. Immunol.* 154:4434–43 (1995).
Ryser, H. J. P., PCT Pub. No. WO 79/00515 (1979).
Simon et al., *Proc. Natl. Acad. Sci.* 89:9367 (1992).
Suffness, M., Ed., *Taxol: Science and Applications*, CRC Press, New York, N.Y., pp. 237–239 (1995).
Shaheen et al., *J. Virology* 70:3392 (1996).
Tavladoraki et al., *Nature* 366:469 (1993).
Thompson, L. A., and Ellman, J. A., *Chem. Rev.* 96:555 (1996).
Wong, S. S., Ed., *Chemistry of Protein Conjugation and Cross-Linking*, CRC Press, Inc., Boca Raton, Fla (1991).
Zuckermann, R. N., *Chemtracts-Macromol. Chem.* 4:80 (1993).

All references cited within this application are incorporated herein by references.

BACKGROUND OF THE INVENTION

The plasma membranes of cells present a barrier to passage of many useful therapeutic agents. In general, a drug must be freely soluble in both the aqueous compartments of the body and the lipid layers through which it must pass, in order to enter cells. Highly charged molecules in particular experience difficulty in passing across membranes. Many therapeutic macromolecules such as peptides and oligonucleotides are also particularly intractable to transmembrane transport. Thus, while biotechnology has made available a greater number of potentially valuable therapeutics, bioavailability considerations often hinder their medicinal utility. There is therefore a need for reliable means of transporting drugs, and particularly macromolecules, into cells.

Heretofore, a number of transporter molecules have been proposed to escort molecules across biological membranes. Ryser et al. (1979) teaches the use of high molecular weight polymers of lysine for increasing transport of various molecules across cellular membranes, with very high molecular weights being preferred. Although the authors contemplated polymers of other positively charged residues such as ornithine and arginine, operativity of such polymers was not shown.

Barsoum et al. (1994) and Fawell et al. (1994) proposed using shorter fragments of the tat protein containing the tat basic region (residues 49–57 having the sequence RKKRRQRRR (SEQ ID NO: 1). Barsoum et al. noted that moderately long polyarginine polymers (MW 5000–15000 datons) failed to enable transport of .beta.-galactosidase across cell membranes (e.g., Barsourm on page 3), contrary to the suggestion of Ryser et al. (supra).

Other studies have shown that a 16 amino acid peptide-cholesterol conjugate derived from the Antennapedia homeodomain is rapidly internalized by cultured neurons (Brugidou et al., 1995). However, slightly shorter versions of this peptide (is residues) are not effectively taken up by cells (Derossi et al., 1996).

The present invention is based in part on the applicants' discovery that conjugation of certain polymers composed of contiguous, highly basic subunits, particularly subunits containing guanidyl or amidinyl moieties, to small molecules or macromolecules is effective to significantly enhance transport of the attached molecule across biological membranes. Moreover, transport occurs at a rate significantly greater than the transport rate provided by a basic HIV tat peptide consisting of residues 49–57 (SEQ ID NO: 1).

SUMMARY OF THE INVENTION

The present invention includes, in one aspect, a method for enhancing transport of a selected compound across a biological membrane. In the method, a biological membrane is contacted with a conjugate containing a biologically active agent that is covalently attached to at least one transport polymer. The conjugate is effective to promote transport of the agent across the biological membrane at a rate that is greater than the trans-membrane transport rate of the biological agent in non-conjugated form.

In one embodiment, the polymer consists of from 6 to 25 subunits, at least 50% of which contain a guanidino or amidino sidechain moiety, wherein the polymer contains at least 6, and more preferably, at least 7 guanidino or amidino sidechain moieties. In another embodiment, the polymer consists of from 6 to 20, 7 to 20, or 7 to 15 subunits. More preferably, at least 70% of the subunits in the polymer contain guanidino or amidino sidechain moiety, and more preferably still, 90%. Preferably, no guanidino or amidino sidechain moiety is separated from another such moiety by more than one non-guanidino or non-amidino subunit. In a more specific embodiment, the polymer contains at least 6 contiguous subunits each containing either a guanidino or amidino group, and preferably at least 6 or 7 contiguous guanidino sidechain moieties.

In another embodiment, the transport polymer contains from 6 to 25 contiguous subunits, from 7 to 25, from 6 to 20, or preferably from 7 to 20 contiguous subunits, each of which contains a guanidino or amidino sidechain moiety, and with the optional proviso that one of the contiguous subunits can contain a non-arginine residue to which the agent is attached.

In one embodiment, each contiguous subunit contains a guanidino moiety, as exemplified by a polymer containing at least six contiguous arginine residues.

Preferably, each transport polymer is linear. In a preferred embodiment, the agent is attached to a terminal end of the transport polymer.

In another specific embodiment, the conjugate contains a single transport polymer.

The transport-enhancing polymers are exemplified, in a preferred embodiment, by peptides in which arginine residues constitute the subunits. Such a polyarginine peptide may be composed of either all D-, all L- or mixed D- and L-arginines, and may include additional amino acids. More preferably, at least one, and preferably all of the subunits are D-arginine residues, to enhance biological stability of the polymer during transit of the conjugate to its biological target.

The method may be used to enhance transport of selected therapeutic agents across any of a number of biological membranes including, but not limited to, eukaryotic cell membranes, prokaryotic cell membranes, and cell walls. Exemplary prokaryotic cell membranes include bacterial membranes. Exemplary eukaryotic cell membranes of interest include, but are not limited to membranes of dendritic cells, epithelial cells, endothelial cells, keratinocytes, muscle cells, fungal cells, bacterial cells, plant cells, and the like.

According to a preferred embodiment of the invention, the transport polymer of the invention has an apparent affinity (Km) that is at least 10-fold greater, and preferably at least 100-fold greater, than the affinity measured for tat(49–75) peptide by the procedure of Example 6 when measured at room temperature (23° C.) or 37° C.

Biologically active agents (which encompass therapeutic agents) include, but are not limited to metal ions, which are typically delivered as metal chelates; small organic molecules, such anticancer (e.g., taxane) and antimicrobial molecules (e.g., against bacteria or fungi such as yeast); and macromolecules such as nucleic acids, peptides, proteins, and analogs thereof. In one preferred embodiment, the agent is a nucleic acid or nucleic acid analog, such as a ribozyme which optionally contains one or more 2'-deoxy nucleotide subunits for enhanced stability. Alternatively, the agent is a peptide nucleic acid (PNA). In another preferred embodiment, the agent is a polypeptide, such as a protein antigen, and the biological membrane is a cell membrane of an antigen-presenting cell (APC). In another embodiment, the agent is selected to promote or elicit an immune response against a selected tumor antigen. In another preferred embodiment, the agent is a taxane or taxoid anticancer compound. In another embodiment, the agent is a non-polypeptide agent, preferably a non-polypeptide therapeutic agent. In a more general embodiment, the agent preferably has a molecular weight less than 10 kDa.

The agent may be linked to the polymer by a linking moiety, which may impart conformational flexibility within the conjugate and facilitate interactions between the agent and its biological target. In one embodiment, the linking moiety is a cleavable linker, e.g., containing a linker group that is cleavable by an enzyme or by solvent-mediated cleavage, such as an ester, amide, or disulfide group. In another embodiment, the cleavable linker contains a photo-cleavable group.

In a more specific embodiment, the cleavable linker contains a first cleavable group that is distal to the biologically active agent, and a second cleavable group that is proximal to the agent, such that cleavage of the first cleavable group yields a linker-agent conjugate containing a nucleophilic moiety capable of reacting intramolecularly to cleave the second cleavable group, thereby releasing the agent from the linker and polymer.

In another embodiment, the invention can be used to screen a plurality of conjugates for a selected biological activity, wherein the conjugates are formed from a plurality of candidate agents. The conjugates are contacted with a cell that exhibits a detectable signal upon uptake of the conjugate into the cell, such that the magnitude of the signal is indicative of the efficacy of the conjugate with respect to the selected biological activity. This method is particularly useful for testing the activities of agents that by themselves are unable, or poorly able, to enter cells to manifest biological activity. In one embodiment, the candidate agents are selected from a combinatorial library.

The invention also includes a conjugate library which is useful for screening in the above method.

In another aspect, the invention includes a pharmaceutical composition for delivering a biologically active agent across a biological membrane. The composition comprises a conjugate containing a biologically active agent covalently attached to at least one transport polymer as described above, and a pharmaceutically acceptable excipient. The polymer is effective to impart to the agent a rate of trans-membrane transport that is greater than the trans-membrane transport rate of the agent in non-conjugated form. The composition may additionally be packaged with instructions for using it.

In another aspect, the invention includes a therapeutic method for treating a mammalian subject, particularly a human subject, with a pharmaceutical composition as above.

These and other objects and features of the invention will become more fully apparent when the following detailed description of the invention is read in conjunction with the accompanying drawings.

BRIEF DESCRIPTION OF THE DRAWINGS

FIGS. 1A and 1B are plots of cellular uptake of certain polypeptide-fluorescein conjugates containing tat basic peptide (49–57, SEQ ID NO:1), poly-Lys (K9, SEQ ID NO:2), and poly-Arg (R4–R9 and r4–r9, SEQ ID NO:3–8 and 12–17, respectively), as a function of peptide concentration; FIG. 1C is a histogram of uptake levels of the conjugates measured for conjugates at a concentration of 12.5 $\mu$M (Examples 2–3);

FIGS. 2A–2F show computer-generated images of confocal micrographs (Example 4) showing emitted fluorescence (2A–2C) and transmitted light (2D–2F) from Jurkat cells after incubation at 37° C. for 10 minutes with 6.25 $\mu$M of tat (49–57) conjugated to fluorescein (panels A and D), a 7-mer of poly-L-arginine (R7) labeled with fluorescein (panels B and E), or a 7-mer of poly-D-arginine (r7) labeled with fluorescein (panels C and F);

FIG. 5A compares uptake levels observed for R9 and r9 conjugates as a function of conjugate concentration, when incubated with *E. coli* HB 101 cells; FIG. 5B shows uptake levels observed for K9 and r4 to r9 conjugates when incubated with *E. coli* HB 101 cells; FIG. 5C compares uptake levels of conjugates of r9 and K9 when incubated with *Strep. Bovis* cells;

DETAILED DESCRIPTION OF THE INVENTION

I. Definitions

Figure 3:
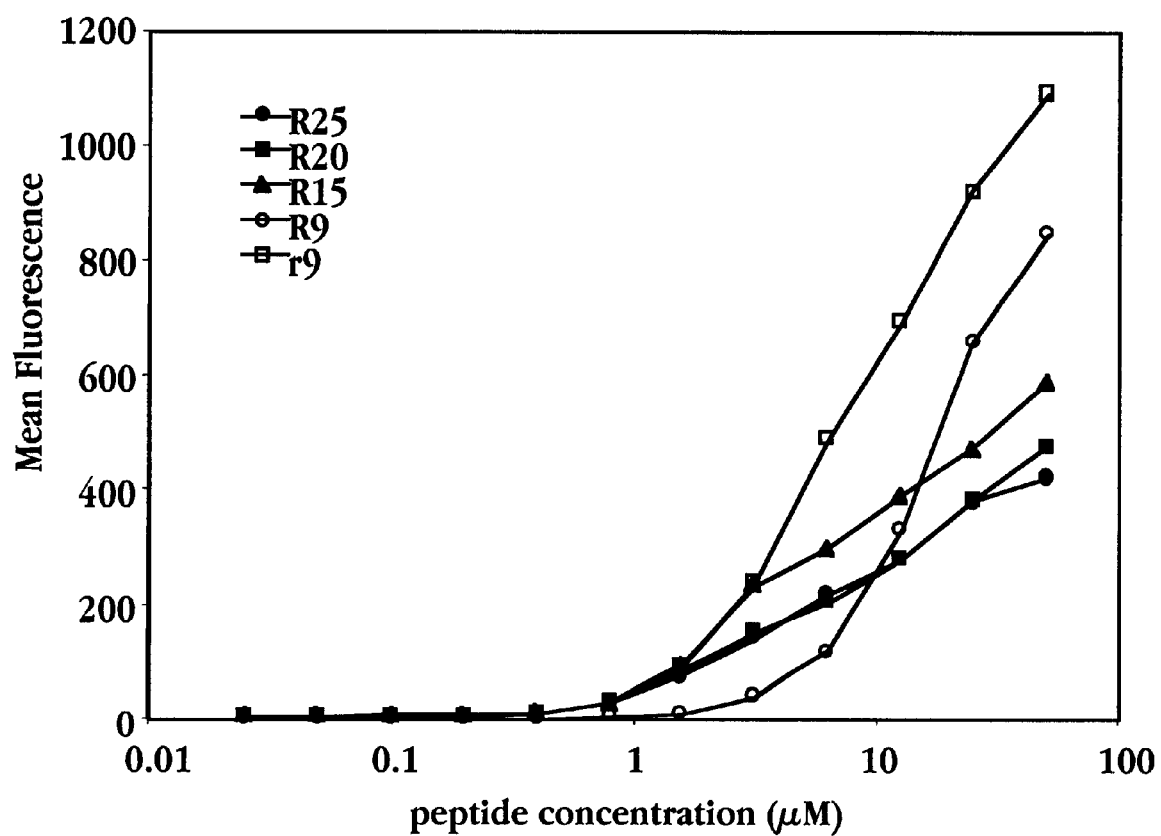
FIG. 3 shows cellular uptake of certain poly-Arg-fluorescein conjugates (r9, R9, R15, R20, and R25, SEQ ID NO: 17 and 8–11, respectively) as a function of conjugate concentration (Example 5)

The term "biological membrane" as used herein refers to a lipid-containing barrier which separates cells or groups of cells from the extracellular space. Biological membranes include, but are not limited to, plasma membranes, cell walls, intracellular organelle membranes, such as the mitochondrial membrane, nuclear membranes, and the like.

The term "transmembrane concentration" refers to the concentration of a compound present on the side of a membrane that is opposite or "trans" to the side of the membrane to which a particular composition has been added. For example, when a compound is added to the extracellular fluid of a cell, the amount of the compound measured subsequently inside the cell is the transmembrane concentration of the compound.

"Biologically active agent" or "biologically active substance" refers to a chemical substance, such as a small molecule, macromolecule, or metal ion, that causes an observable change in the structure, function, or composition of a cell upon uptake by the cell. Observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased or decreased rate of synthesis of a metabolite, increased or decreased cell proliferation, and the like.

The term "macromolecule" as used herein refers to large molecules (MW greater than 1000 daltons) exemplified by, but not limited to, peptides, proteins, oligonucleotide and polynucleotides of biological or synthetic origin.

"Small organic molecule" refers to a carbon-containing agent having a molecular weight (MW) of less than or equal to 1000 daltons.

The terms "therapeutic agent", "therapeutic composition", and "therapeutic substance" refer, without limitation, to any composition that can be used to the benefit of a mammalian species. Such agents may take the form of ions, small organic molecules, peptides, proteins or polypeptides, oligonucleotides, and oligosaccharides, for example.

The terms "non-polypeptide agent" and "non-polypeptide therapeutic agent" refer to the portion of a transport polymer conjugate that does not include the transport-enhancing polymer, and that is a biologically active agent other than a polypeptide. An example of a non-polypeptide agent is an anti-sense oligonucleotide, which can be conjugated to a poly-arginine peptide to form a conjugate for enhanced delivery across biological membranes.

The term "polymer" refers to a linear chain of two or more identical or non-identical subunits joined by covalent bonds. A peptide is an example of a polymer that can be composed of identical or non-identical amino acid subunits that are joined by peptide linkages.

The term "peptide" as used herein refers to a compound made up of a single chain of D- or L-amino acids or a mixture of D- and L-amino acids joined by peptide bonds. Generally, peptides contain at least two amino acid residues and are less than about 50 amino acids in length.

The term "protein" as used herein refers to a compound that is composed of linearly arranged amino acids linked by peptide bonds, but in contrast to peptides, has a well-defined conformation. Proteins, as opposed to peptides, generally consist of chains of 50 or more amino acids.

"Polypeptide" as used herein refers to a polymer of at least two amino acid residues and which contains one or more peptide bonds. "Polypeptide" encompasses peptides and proteins, regardless of whether the polypeptide has a well-defined conformation.

The terms "guanidyl", "guanidinyl", and "guanidino" are used interchangeably to refer to a moiety having the formula —HN=C (NH$_2$)NH (unprotonated form). As an example, arginine contains a guanidyl (guanidino) moiety, and is also referred to as 2-amino-5-guanidinovaleric acid or α-amino-δ-guanidinovaleric acid. "Guanidinium" refers to the positively charged conjugate acid form.

"Amidinyl" and "amidino" refer to a moiety having the formula —C(=NH) (NH$_2$). "Amidinium" refers to the positively charged conjugate acid form.

The term "poly-arginine" or "poly-Arg" refers to a polymeric sequence composed of contiguous arginine residues; poly-L-arginine refers to all L-arginines; poly-D-arginine refers to all D-arginines. Poly-L-arginine is also abbreviated by an upper case "R" followed by the number of L-arginines in the peptide (e.g., R8 represents an 8-mer of contiguous L-arginine residues); poly-D-arginine is abbreviated by a lower case "r" followed by the number of D-arginines in the peptide (r8 represents an 8-mer of contiguous D-arginine residues).

Amino acid residues are referred to herein by their full names or by standard single-letter or three-letter notations: A, Ala, alanine; C, Cys, cysteine; D, Asp, aspartic acid; E, Glu, glutamic acid; F, Phe, phenylalanine; G, Gly, glycine; H, His, histidine; I, Ile, isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; Y, Tyr, tyrosine.

II. Structure of Polymer Moiety

In one embodiment, transport polymers in accordance with the present invention contain short-length polymers of from 6 to up to 25 subunits, as described above. The conjugate is effective to enhance the transport rate of the conjugate across the biological membrane relative to the transport rate of the non-conjugated biological agent alone. Although exemplified polymer compositions are peptides, the polymers may contain non-peptide backbones and/or subunits as discussed further below.

In an important aspect of the invention, the conjugates of the invention are particularly useful for transporting biologically active agents across cell or organelle membranes, when the agents are of the type that require trans-membrane transport to exhibit their biological effects, and that do not exhibit their biological effects primarily by binding to a surface receptor, i.e., such that entry of the agent does not occur. Further, the conjugates are particularly useful for transporting biologically active agents of the type that require trans-membrane transport to exhibit their biological effects, and that by themselves (without conjugation to a transport polymer or some other modification), are unable, or only poorly able, to enter cells to manifest biological activity.

As a general matter, the transport polymer used in the conjugate preferably includes a linear backbone of subunits. The backbone will usually comprise heteroatoms selected from carbon, nitrogen, oxygen, sulfur, and phosphorus, with the majority of backbone chain atoms usually consisting of carbon. Each subunit contains a sidechain moiety that includes a terminal guanidino or amidino group.

Although the spacing between adjacent sidechain moieties will usually be consistent from subunit to subunit, the polymers used in the invention can also include variable spacing between sidechain moieties along the backbone.

The sidechain moieties extend away from the backbone such that the central guanidino or amidino carbon atom (to which the $NH_2$ groups are attached) is linked to the backbone by a sidechain linker that preferably contains at least 2 linker chain atoms, more preferably from 2 to 5 chain atoms, such that the central carbon atom is the third to sixth chain atom away from the backbone. The chain atoms are preferably provided as methylene carbon atoms, although one or more other atoms such as oxygen, sulfur, or nitrogen can also be present. Preferably, the sidechain linker between the backbone and the central carbon atom of the guanidino or amidino group is 4 chain atoms long, as exemplified by an arginine side chain.

The transport polymer sequence of the invention can be flanked by one or more non-guanidino/non-amidino subunits, or a linker such as an aminocaproic acid group, which do not significantly affect the rate of membrane transport of the corresponding polymer-containing conjugate, such as glycine, alanine, and cysteine, for example. Also, any free amino terminal group can be capped with a blocking group, such as an acetyl or benzyl group, to prevent ubiquitination in vivo.

The agent to be transported can be linked to the transport polymer according to a number of embodiments. In one preferred embodiment, the agent is linked to a single transport polymer, either via linkage to a terminal end of the transport polymer or to an internal subunit within the polymer via a suitable linking group.

In a second embodiment, the agent is attached to more than one polymer, in the same manner as above. This embodiment is somewhat less preferred, since it can lead to crosslinking of adjacent cells.

In a third embodiment, the conjugate contains two agent moieties attached to each terminal end of the polymer. For this embodiment, it is preferred that the agent has a molecular weight of less than 10 kDa.

With regard to the first and third embodiments just mentioned, the agent is generally not attached to one any of the guanidino or amidino sidechains so that they are free to interact with the target membrane.

The conjugates of the invention can be prepared by straightforward synthetic schemes. Furthermore, the conjugate products are usually substantially homogeneous in length and composition, so that they provide greater consistency and reproducibility in their effects than heterogeneous mixtures.

According to an important aspect of the present invention, it has been found by the applicants that attachment of a single transport polymer to any of a variety of types of biologically active agents is sufficient to substantially enhance the rate of uptake of an agent across biological membranes, even without requiring the presence of a large hydrophobic moiety in the conjugate. In fact, attaching a large hydrophobic moiety may significantly impede or prevent cross-membrane transport due to adhesion of the hydrophobic moiety to the lipid bilayer. Accordingly, the present invention includes conjugates that do not contain large hydrophobic moieties, such as lipid and fatty acid molecules. In another embodiment, the method is used to treat a non-central nervous system (non-CNS) condition in a subject that does not require delivery through the blood brain barrier.

A. Polymer Components

Amino acids. In one embodiment, the transport polymer is composed of D or L amino acid residues. Use of naturally occurring L-amino acid residues in the transport polymers has the advantage that break-down products should be relatively non-toxic to the cell or organism. Preferred amino acid subunits are arginine ($\alpha$-amino-$\delta$-guanidinovaleric acid) and $\alpha$-amino-$\epsilon$-amidinohexanoic acid (isosteric amidino analog). The guanidinium group in arginine has a pKa of about 12.5.

More generally, it is preferred that each polymer subunit contains a highly basic sidechain moiety which (i) has a pKa of greater than 11, more preferably 12.5 or greater, and (ii) contains, in its protonated state, at least two geminal amino groups ($NH_2$) which share a resonance-stabilized positive charge, which gives the moiety a bidentate character.

Other amino acids, such as $\alpha$-amino-$\beta$-guanidino-propionic acid, $\alpha$-amino-$\gamma$-guanidinobutyric acid, or $\alpha$-amino-$\epsilon$-guanidinocaproic acid can also be used (containing 2, 3 or 5 linker atoms, respectively, between the backbone chain and the central guanidinium carbon).

D-amino acids may also be used in the transport polymers. Compositions containing exclusively D-amino acids have the advantage of decreased enzymatic degradation. However, they may also remain largely intact within the target cell. Such stability is generally not problematic if the agent is biologically active when the polymer is still attached. For agents that are inactive in conjugate form, a linker that is cleavable at the site of action (e.g., by enzyme- or solvent-mediated cleavage within a cell) should be included within the conjugate to promote release of the agent in cells or organelles.

Other Subunits. Subunits other than amino acids may also be selected for use in forming transport polymers. Such subunits may include, but are not limited to hydroxy amino acids, N-methyl-amino acids amino aldehydes, and the like, which result in polymers with reduced peptide bonds. Other subunit types can be used, depending on the nature of the selected backbone, as discussed in the next section.

B. Backbone Type

A variety of backbone types can be used to order and position the sidechain guanidino and/or amidino moieties, such as alkyl backbone moieties joined by thioethers or sulfonyl groups, hydroxy acid esters (equivalent to replacing amide linkages with ester linkages), replacing the alpha carbon with nitrogen to form an aza analog, alkyl backbone moieties joined by carbamate groups, polyethyleneimines (PEIs), and amino aldehydes, which result in polymers composed of secondary amines.

A more detailed backbone list includes N-substituted amide (CONR replaces CONH linkages), esters ($CO_2$), ketomethylene ($COCH_2$) reduced or methyleneamino ($CH_2NH$), thioamide (CSNH), phosphinate ($PO_2RCH_2$), phosphonamidate and phosphonamidate ester ($PO_2RNH$), retropeptide (NHCO), trans-alkene (CR=CH), fluoroalkene (CF=CH), dimethylene ($CH_2CH_2$), thioether ($CH_2S$), hydroxyethylene ($CH(OH)CH_2$), methyleneoxy ($CH_2O$), tetrazole ($CN_4$), retrothioamide (NHCS), retroreduced ($NHCH_2$), sulfonamido ($SO_2NH$), methylenesulfonamido ($CHRSO_2NH$), retrosulfonamide ($NHSO_2$), and peptoids (N-substituted glycines), and backbones with malonate and/or gem-diaminoalkyl subunits, for example, as reviewed by Fletcher et al. (1998) and detailed by references cited therein. Peptoid backbones (N-substituted glycines) can also be used (e.g., Kessler, 1993; Zuckermann et al., 1992; and Simon et al., 1992). Many of the foregoing substitutions result in approximately isosteric polymer backbones relative to backbones formed from α-amino acids.

Studies carried out in support of the present invention have utilized polypeptides (e.g., peptide backbones). However, other backbones, such as those described above, may provide enhanced biological stability (for example, resistance to enzymatic degradation in vivo).

C. Synthesis of Polymeric Transport Molecules

Polymers are constructed by any method known in the art. Exemplary peptide polymers can be produced synthetically, preferably using a peptide synthesizer (Applied Biosystems Model 433) or can be synthesized recombinantly by methods well known in the art. Recombinant synthesis is generally used when the transport polymer is a peptide which is fused to a polypeptide or protein of interest.

N-methyl and hydroxy-amino acids can be substituted for conventional amino acids in solid phase peptide synthesis. However, production of polymers with reduced peptide bonds requires synthesis of the dimer of amino acids containing the reduced peptide bond. Such dimers are incorporated into polymers using standard solid phase synthesis procedures. Other synthesis procedures are well known and can be found, for example, in Fletcher et al. (1998), Simon et al. (1992), and references cited therein.

III. Attachment of Transport Polymers to Biologically Active Agents

Transport polymers of the invention can be attached covalently to biologically active agents by chemical or recombinant methods.

A. Chemical Linkages Biologically active agents such as small organic molecules and macromolecules can be linked to transport polymers of the invention via a number of methods known in the art (see, for example, Wong, 1991), either directly (e.g., with a carbodiimide) or via a linking moiety. In particular, carbamate, ester, thioether, disulfide, and hydrazone linkages are generally easy to form and suitable for most applications. Ester and disulfide linkages are preferred if the linkage is to be readily degraded in the cytosol, after transport of the substance across the cell membrane.

Various functional groups (hydroxyl, amino, halogen, etc.) can be used to attach the biologically active agent to the transport polymer. Groups which are not known to be part of an active site of the biologically active agent are preferred, particularly if the polypeptide or any portion thereof is to remain attached to the substance after delivery.

Polymers, such as peptides produced according to Example 1, are generally produced with an amino terminal protecting group, such as FMOC. For biologically active agents which can survive the conditions used to cleave the polypeptide from the synthesis resin and deprotect the sidechains, the FMOC may be cleaved from the N-terminus of the completed resin-bound polypeptide so that the agent can be linked to the free N-terminal amine. In such cases, the agent to be attached is typically activated by methods well known in the art to produce an active ester or active carbonate moiety effective to form an amide or carbamate linkage, respectively, with the polymer amino group. Of course, other linking chemistries can also be used.

To, help minimize side-reactions, guanidino and amidino moieties can be blocked using conventional protecting groups, such as carbobenzyloxy groups (CBZ), di-t-BOC, PMC, Pbf, N-NO2, and the like.

Coupling reactions are performed by known coupling methods in any of an array of solvents, such as N,N-dimethyl formamide (DMF), N-methyl pyrrolidinone, dichloromethane, water, and the like. Exemplary coupling reagents include O-benzotriazolyloxy tetramethyluronium hexafluorophosphate (HATU), dicyclohexyl carbodiimide, bromo-tris (pyrrolidino) phosphonium bromide (PyBroP), etc. Other reagents can be included, such as N,N-dimethylamino pyridine (DMAP), 4-pyrrolidino pyridine, N-hydroxy succinimide, N-hydroxy benzotriazole, and the like.

For biologically active agents that are inactive until the attached transport polymer is released, the linker is preferably a readily cleavable linker, meaning that it is susceptible to enzymatic or solvent-mediated cleavage in vivo. For this purpose, linkers containing carboxylic acid esters and disulfide bonds are preferred, where the former groups are hydrolyzed enzymatically or chemically, and the latter are severed by disulfide exchange, e.g., in the presence of glutathione.

In one preferred embodiment, the cleavable linker contains a first cleavable group that is distal to the agent, and a second cleavable group that is proximal to the agent, such that cleavage of the first cleavable group yields a linker-agent conjugate containing a nucleophilic moiety capable of reacting intramolecularly to cleave the second cleavable group, thereby releasing the agent from the linker and polymer. This embodiment is further illustrated by the various small molecule conjugates discussed below.

B. Fusion Polypeptides

Transport peptide polymers of the invention can be attached to biologically active polypeptide agents by recombinant means by constructing vectors for fusion proteins comprising the polypeptide of interest and the transport peptide, according to methods well known in the art. Generally, the transport peptide component will be attached at the C-terminus or N-terminus of the polypeptide of interest, optionally via a short peptide linker.

IV. Enhanced Transport of Biologically Active Agents Across Biological Membranes A. Measuring Transport Across Biological Membranes Model systems for assessing the ability of polymers of the invention to transport biomolecules and other therapeutic substances across biological membranes include systems that measure the ability of the polymer to transport a covalently attached fluorescent molecule across the membrane. For example, fluorescein (≈376 MW) can serve as a model for transport of small organic molecules (Example 2).

For transport of macromolecules, a transport polymer can be fused to a large polypeptide such as ovalbumin (molecular weight 45 kDa; e.g., Example 14). Detecting uptake of macromolecules may be facilitated by attaching a fluorescent tag. Cellular uptake can also be analyzed by confocal microscopy (Example 4).

B. Enhanced Transport Across Biological Membranes

In experiments carried out in support of the present invention, transmembrane transport and concomitant cellular uptake was assessed by uptake of a transport peptide linked to fluorescein, according to methods described in Examples 2 and 3. Briefly, suspensions of cells were incubated with fluorescent conjugates suspended in buffer for varying times at 37° C., 23° C., or 3° C. After incubation, the reaction was stopped and the cells were collected by centrifugation and analyzed for fluorescence using fluorescence-activated cell sorting (FACS).

Under the conditions used, cellular uptake of the conjugates was not saturable. Consequently, $ED_{50}$ values could not be calculated for the peptides. Instead, data are presented as histograms to allow direct comparisons of cellular uptake at single conjugate concentrations.

FIGS. 1A–1C show results from a study in which polymers of L-arginine (R; FIG. 1A) or D-arginine (r; FIG. 1B) ranging in length from 4 to 9 arginine subunits were tested for ability to transport fluorescein into Jurkat cells. For comparison, transport levels for an HIV tat residues 49–57 ("49–57") and a nonamer of L-lysine (K9) were also tested. FIG. 1C shows a histogram of uptake levels for the conjugates at a concentration of 12.5 $\mu$M.

As shown in the figures, fluorescently labeled peptide polymers composed of 6 or more arginine residues entered cells more efficiently than the tat sequence 49–57. In particular, uptake was enhanced to at least about twice the uptake level of tat 49–57, and as much as about 6–7 times the uptake level of tat 49–57. Uptake of fluorescein alone was negligible. Also, the lysine nonamer (K9) showed very little uptake, indicating that short lysine polymers are ineffective as trans-membrane transports, in contrast to comparable-length guanidinium-containing polymers.

With reference to FIG. 1B, homopolymers of D-arginine exhibited even greater transport activity than the L-counterparts. However, the order of uptake levels was about the same. For the D-homopolymers, the peptides with 7 to 9 arginines exhibited roughly equal activity. The hexamer (R6 or r6) was somewhat less effective, but still exhibited at least about 2 to 3-fold higher transport activity than tat(49–57).

The ability of the D- and L-arginine polymers to enhance trans-membrane transport was confirmed by confocal microscopy (FIGS. 2A–2F and Example 4). Consistent with the FACS data described above, the cytosol of cells incubated with either R9 (FIGS. 2B and 2E) or r9 (FIGS. 2C and 2F) was brightly fluorescent, indicating high levels of conjugate transport into the cells. In contrast, tat(49–57) at the same concentration showed only weak staining (FIGS. 2A and 2D). The confocal micrographs also emphasize the point that the D-arginine polymer (FIG. 2C) was more effective at entering cells than the polymer composed of L-arginine (FIG. 2F).

From the foregoing, it is apparent that transport polymers of the invention are significantly more effective than HIV tat peptide 47–59 in transporting drugs across the plasma membranes of cells. Moreover, the poly-Lys nonamer was ineffective as a transporter.

To determine whether there was an optimal length for contiguous guanidinium-containing homopolymers, a set of longer arginine homopolymer conjugates (R15, R20, R25, and R30) were examined. To examine the effect of substantially longer polymers, a mixture of L-arginine polymers with an average molecular weight of 12,000 daltons ($\approx$100 amino acids) was also tested (Example 5). However, to avoid precipitation problems, the level of serum in the assay had to be reduced for testing conjugates with the $\approx$12,000 MW polymer material. Cell uptake was analyzed by FACS as above, and the mean fluorescence of live cells was measured. Cytotoxicity of each conjugate was also measured.

With reference to FIG. 3, uptake of L-arginine homopolymer conjugates with 15 or more arginines exhibited patterns of cellular uptake distinctly different from polymers containing nine arginines or less. The curves of the longer conjugates were flatter, crossing those of the R9 and r9 conjugates. At higher concentrations (>3 $\mu$M), uptake of R9 and r9 was significantly better than for the longer polymers. However, at lower concentrations, cells incubated with the longer peptides exhibited greater fluorescence.

Based on this data, it appears that r9 and R9 enter the cells at higher rates than polymers containing 15 or more contiguous arginines. However, the biological half-life of R9 (L-peptide) was shorter than for the longer conjugates, presumably because proteolysis of the longer peptides (due to serum enzymes) produces fragments that retain transport activity. In contrast, the D-isomer (r9) did not show evidence of proteolytic degradation, consistent with the high specificity of serum proteases for L-polypeptides.

Thus, overall transport efficacy of a transport polymer appears to depend on a combination of (i) rate of transmembrane uptake (polymer with less than about 15 continuous arginines are better) versus susceptibility to proteolytic inactivation (longer polymers are better). Accordingly, polymers containing 7 to 20 contiguous guanidinium residues, and preferably 7 to 15, are preferred.

Notably, the high molecular weight polyarginine conjugate (12,000 MW) did not exhibit detectable uptake. This result is consistent with the observations of Barsoum et al. (1994), and suggests that arginine polymers have transport properties that are significantly different from those that may be exhibited by lysine polymers. Furthermore, the 12,000 polyarginine conjugate was found to be highly toxic (Example 5). In general, toxicity of the polymers increased with length, though only the 12,000 MW conjugate showed high toxicity at all concentrations tested.

When cellular uptake of polymers of D- and L-arginine were analyzed by Michaelis-Menten kinetics (Example 6), the rate of uptake by Jurkat cells was so efficient that precise $K_m$ values could only be obtained when the assays were carried out at 3° C. (on ice). Both the maximal rate of transport ($V_{max}$) and the apparent affinity of the peptides for the putative receptor of the Michaelis constant ($K_m$) were derived from Lineweaver-Burk plots of the observed fluorescence of Jurkat cells after incubation with varying concentrations of nonamers of D- and L-arginine for 30, 60, 120, and 240 seconds.

Kinetic analysis also reveals that polymers rich in arginine exhibit a better ability to bind to and traverse a putative cellular transport site than, for example, the tat(49–57) peptide, since the $K_m$ for transport of the nonameric poly-L-arginine (44 $\mu$M) was substantially lower than the $K_m$ of the tat peptide (722 $\mu$M). Moreover, the nonamer of D-arginine exhibited the lowest Km (7$\mu$M) of the polymers tested in this assay (Table 1), i.e., an approximately 100-fold greater apparent affinity.

According to a preferred embodiment of the invention, the transport polymer of the invention has an apparent affinity (Km) that is at least 10-fold greater, and preferably at least 100-fold greater, than the affinity measured for tat by the procedure of Example 6 when measured at room temperature (23° C.) or 37° C.

TABLE 1

| | $K_M$ ($\mu M$) | $V_{MAX}$ ($\mu M/sec$) |
|---|---|---|
| $H_3N$-RRRRRRRRR-COO$^-$ (SEQ ID NO:8) | 44.43 | 0.35 |
| $H_3N$-rrrrrrrrr-COO$^-$ (SEQ ID NO:17) | 7.21 | 0.39 |
| tat 49–57 (SEQ ID NO:1) | 722 | 0.38 |

Figure 4:
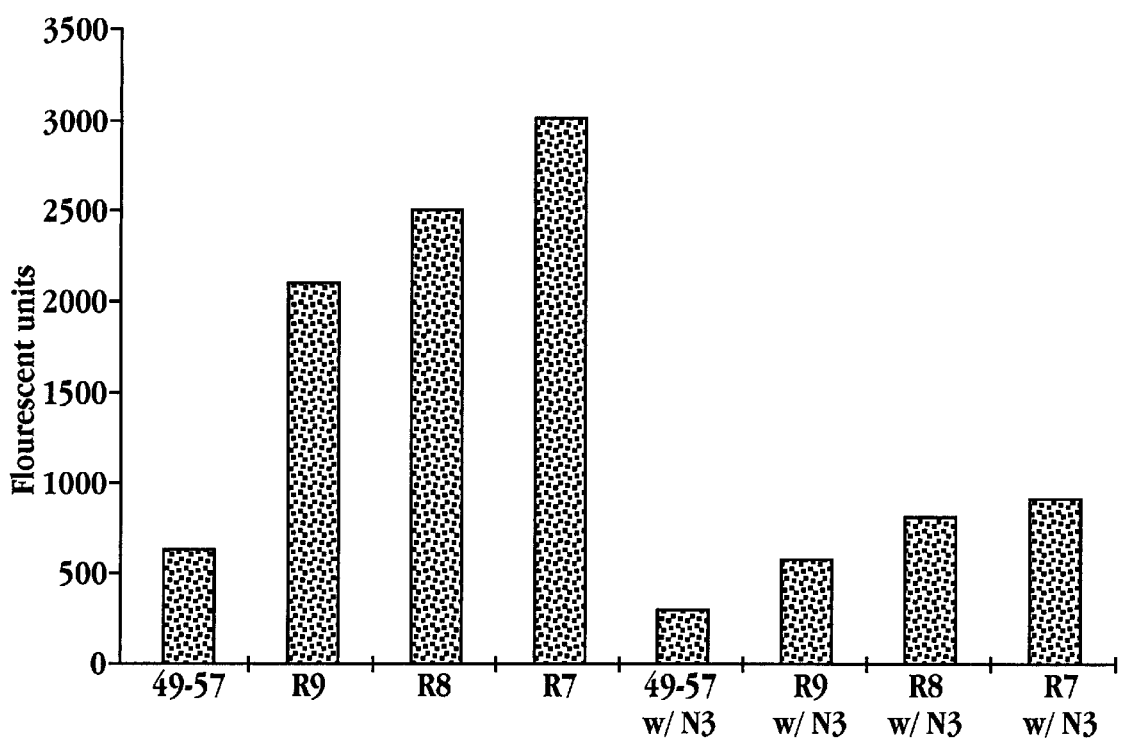
FIG. 4 shows a histogram of cellular uptake of fluorescein-conjugatedtat(49–57), and poly-Arg-fluorescein conjugates (R9, R8, and R7, respectively) in the absence (four bars on left) and presence (four bars on right) of 0.5% sodium azide (Example 7)

Experiments carried out in support of the present invention indicate that polymer-facilitated transport is dependent upon metabolic integrity of cells. Addition of a toxic amount of sodium azide (0.5% w/v) to cells resulted in inhibition of uptake of conjugates by about 90% (Example 7). The results shown in FIG. 4 demonstrate (i) sodium azide sensitivity of trans-membrane transport, suggesting energy-dependence (cellular uptake), and (ii) the superiority of polyguanidinium polymers of the invention (R9, R8, R7) relative to HIV tat(49–57).

Without ascribing to any particular theory, the data suggest that the transport process is an energy-dependent process mediated by specific recognition of guanidinium or amidinium-containing polymers by a molecular transporter present in cellular plasma membranes.

Other experiments in support of the invention have shown that the conjugates of the invention are effective to transport biologically active agents across membranes of a variety of cell types, including human T cells (Jurkat), B cells (murine CH27), lymphoma T cells (murine EL-4), mastocytoma cells (murine P388), several murine T cell hybridomas, neuronal cells (PC-12), fibroblasts (murine RT), kidney cells (murine HELA), myeloblastoma (murine K562); and primary tissue cells, including all human blood cells (except red blood cells), such as T and B lymphocytes, macrophages, dendritic cells, and eiosinophiles; basophiles, mast cells, endothelial cells, cardiac tissue cells, liver cells, spleen cells, lymph node cells, and keratinocytes.

Figure 5A:
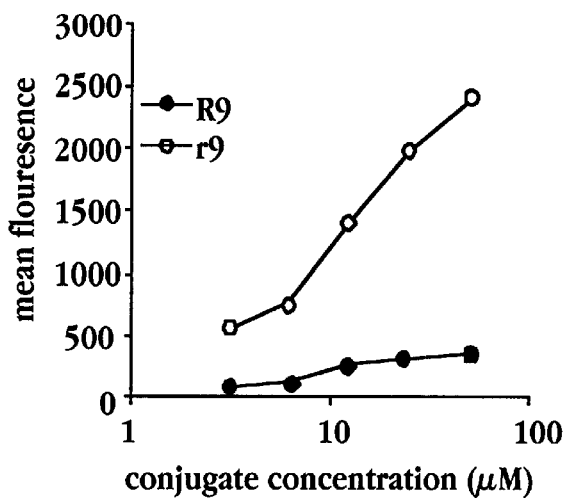
FIGS. 5A–5C show plots of uptake levels of selected polymer conjugates (K9, R9, r4, r5, r6, r7, r8 and r9) by bacterial cells as a function of conjugate concentration.
Figure 5B:
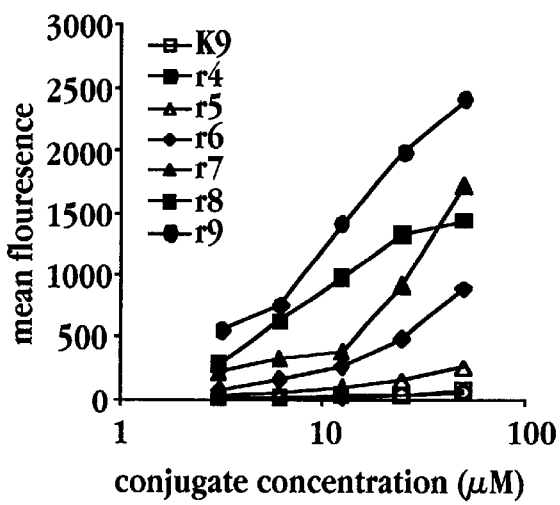
Figure 5C:
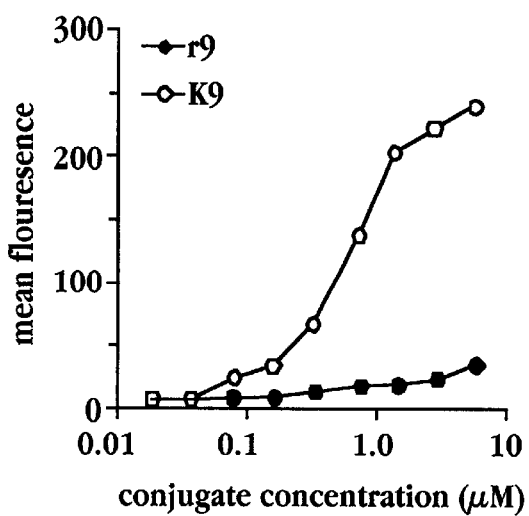

The conjugates are also effective to traverse both gram negative and gram positive bacterial cells, as disclosed in Example 8 and FIGS. 5A–5C. In general, polymers of D-arginine subunits were found to enter both gram-positive and gram-negative bacteria at rates significantly faster than the transport rates observed for polymers of L-arginine. This is illustrated by FIG. 5A, which shows much higher uptake levels for r9 conjugate (D-arginines), than for the R9 conjugate (L-arginines), when incubated with E. coli HB 101 (prokaryotic) cells. This observation may be attributable to proteolytic degradation of the L-polymers by bacterial enzymes.

FIG. 5B shows uptake levels for D-arginine conjugates as a function of length (r4 to r9) in comparison to a poly-L-lysine conjugate (K9), when incubated with E. coli HB 101 cells. As can be seen, the polyarginine conjugates showed a trend similar to that in FIG. 2B observed with eukaryotic cells, such that polymers shorter than r6 showed low uptake levels, with uptake levels increasing as a function of length.

Gram-positive bacteria, as exemplified by Strep. bovis, were also stained efficiently with polymers of arginine, but not lysine, as shown in FIG. 5C.

More generally, maximum uptake levels by the bacteria were observed at 37° C. However, significant staining was observed when incubation was performed either at room temperature or at 3° C. Confocal microscopy revealed that pretreatment of the bacteria with 0.5 sodium azide inhibited transport across the inner plasma membranes of both gram-positive and gram-negative bacteria, but not transport across the cell wall (gram-positive bacteria) into the periplasmic space.

Thus, the invention includes conjugates that contain antimicrobial agents, such as antibacterial and antifungal compounds, for use in preventing or inhibiting microbial proliferation or infection, and for disinfecting surfaces to improve medical safety. In addition, the invention can be used for transport into plant cells, particularly in green leafy plants.

Additional studies in support of the invention have shown that translocation across bacterial membranes is both energy- and temperature-dependent, consistent with observations noted earlier for other cell-types.

V. Therapeutic Compositions

A. Small Organic Molecules

Small organic molecule therapeutic agents may be advantageously attached to linear polymeric compositions as described herein, to facilitate or enhance transport across biological membranes. For example, delivery of highly charged agents, such as levodopa (L-3,4-dihydroxyphenylalanine; L-DOPA) may benefit by linkage to polymeric transport molecules as described herein. Peptoid and peptidomimetic agents are also contemplated (e.g., Langston, 1997; Giannis et al., 1997). Also, the invention is advantageous for delivering small organic molecules that have poor solubilities in aqueous liquids, such as serum and aqueous saline. Thus, compounds whose therapeutic efficacies are limited by their low solubilities can be administered in greater dosages according to the present invention, and can be more efficacious on a molar basis in conjugate form, relative to the non-conjugate form, due to higher uptake levels by cells.

Since a significant portion of the topological surface of a small molecule is often involved, and therefore required, for biological activity, the small molecule portion of the conjugate in particular cases may need to be severed from the attached transport polymer and linker moiety (if any) for the small molecule agent to exert biological activity after crossing the target biological membrane. For such situations, the conjugate preferably includes a cleavable linker for releasing free drug after passing through a biological membrane.

Figure 6A:
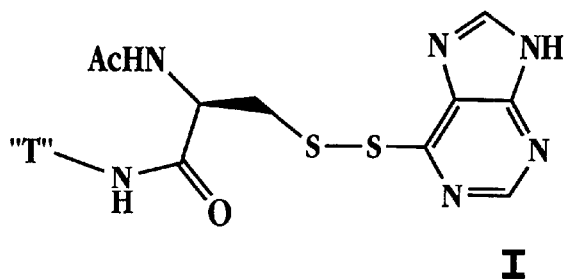
FIGS. 6A–6E show exemplary conjugates of the invention which contain cleavable linker moieties.

In one approach, the conjugate can include a disulfide linkage, as illustrated in FIG. 6A, which shows a conjugate (I) containing a transport polymer T which is linked to a cytotoxic agent, 6-mercaptopurine, by an N-acetyl-protected cysteine group which serves as a linker. Thus, the cytotoxic agent is attached by a disulfide bond to the 6-mercapto group, and the transport polymer is bound to the cysteine carbonyl moiety via an amide linkage. Cleavage of the disulfide bond by reduction or disulfide exchange results in release of the free cytotoxic agent.

A method for synthesizing a disulfide-containing conjugate is provided in Example 9A. The product contains a heptamer of Arg residues which is linked to 6-mercaptopurine by an N-acetyl-Cys-Ala-Ala linker, where the Ala residues are include as an additional spacer to render the disulfide more accessible to thiols and reducing agents for cleavage within a cell. The linker in this example also illustrates the use of amide bonds, which can be cleaved enzymatically within a cell.

In another approach, the conjugate includes a photocleavable linker which is cleaved upon exposure to electromagnetic radiation. An exemplary linkage is illustrated in FIG.

6B, which shows a conjugate (II) containing a transport polymer T which is linked to 6-mercaptopurine via a meta-nitrobenzoate linking moiety. Polymer T is linked to the nitrobenzoate moiety by an amide linkage to the benzoate carbonyl group, and the cytotoxic agent is bound via its 6-mercapto group to the p-methylene group. The compound can be formed by reacting 6-mercaptopurine with p-bromomethyl-m-nitrobenzoic acid in the prescence of NaOCH$_3$/methanol with heating, followed by coupling of the benzoate carboxylic acid to a transport polymer, such as the amino group of a γ-aminobutyric acid linker attached to the polymer (Example 9B). Photo-illumination of the conjugate causes release of the 6-mercaptopurine by virtue of the nitro group that is ortho to the mercaptomethyl moiety. This approach finds utility in phototherapy methods as are known in the art, particularly for localizing drug activation to a selected area of the body.

Preferably, the cleavable linker contains first and second cleavable groups that can cooperate to cleave the polymer from the biologically active agent, as illustrated by the following approaches. That is, the cleavable linker contains a first cleavable group that is distal to the agent, and a second cleavable group that is proximal to the agent, such that cleavage of the first cleavable group yields a linker-agent conjugate containing a nucleophilic moiety capable of reacting intramolecularly to cleave the second cleavable group, thereby releasing the agent from the linker and polymer.

Figure 6B:
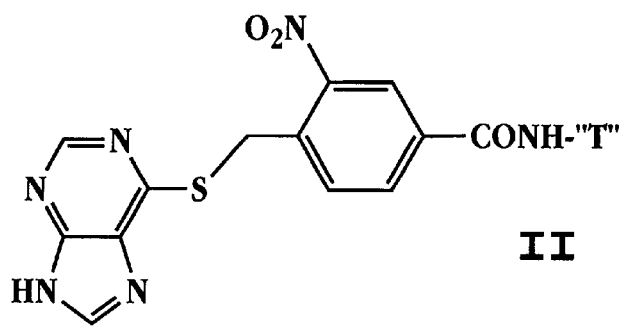
Figure 6C:
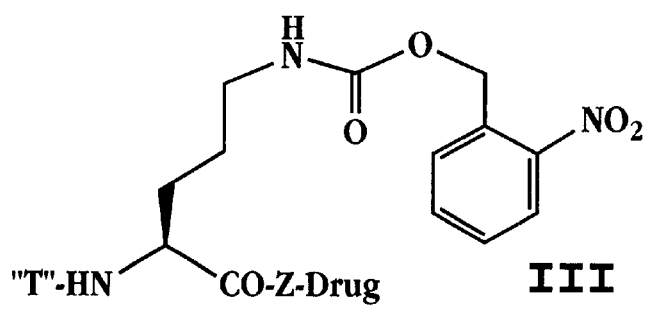

FIG. 6C shows a conjugate (III). containing a transport polymer T linked to the anticancer agent, 5-fluorouracil (5FU). Here, the linkage is provided by a modified lysyl residue. The transport polymer is linked to the α-amino group, and the 5-fluorouracil is linked via the α-carbonyl. The lysyl ε-amino group has been modified to a carbamate ester of o-hydroxymethyl nitrobenzene, which comprises a first, photolabile cleavable group in the conjugate. Photoillumination severs the nitrobenzene moiety from the conjugate, leaving a carbamate which also rapidly decomposes to give the free ε-amino group, an effective nucleophile. Intramolecular reaction of the ε-amino group with the amide linkage to the 5-fluorouracil group leads to cyclization with release of the 5-fluorouracil group.

Figure 6D:
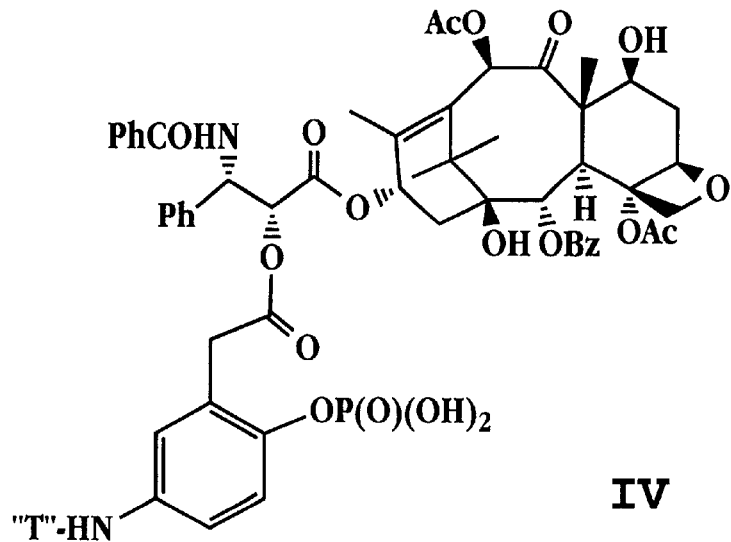

FIG. 6D illustrates a conjugate (IV) containing a transport polymer T linked to 2'-oxygen of the anticancer agent, paclitaxel. The linkage is provided by a linking moiety that includes (i) a nitrogen atom attached to the transport polymer, (ii) a phosphate monoester located para to the nitrogen atom, and (iii) a carboxymethyl group meta to the nitrogen atom, which is joined to the 2'-oxygen of paclitaxel by a carboxylate ester linkage. Enzymatic cleavage of the phosphate group from the conjugate affords a free phenol hydroxyl group. This nucleophilic group then reacts intramolecularly with the carboxylate ester to release free paclitaxel, for binding to its biological target. Example 9C describes a synthetic protocol for preparing this type of conjugate.

Figure 6E:
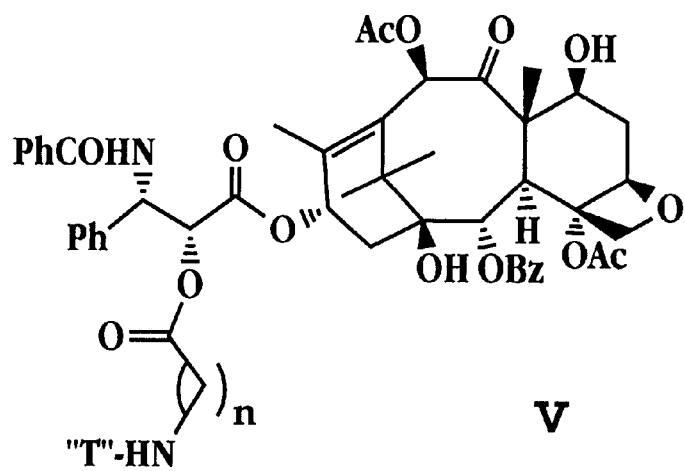

FIG. 6E illustrates yet another approach wherein a transport polymer is linked to a biologically active agent, e.g., paclitaxel, by an aminoalkyl carboxylic acid. Preferably, the linker amino group is linked to the linker carboxyl carbon by from 3 to 5 chain atoms (n=3 to 5), preferably either 3 or 4 chain atoms, which are preferably provided as methylene carbons. As seen in FIG. 6E, the linker amino group is joined to the transport polymer by an amide linkage, and is joined to the paclitaxel moiety by an ester linkage. Enzymatic cleavage of the amide linkage releases the polymer and produces a free nucleophilic amino group. The free amino group can then react intramolecularly with the ester group to release the linker from the paclitaxel.

FIGS. 6D and 6E are illustrative of another aspect of the invention, comprising taxane- and taxoid anticancer conjugates which have enhanced trans-membrane transport rates relative to corresponding non-conjugated forms. The conjugates are particularly useful for inhibiting growth of cancer cells. Taxanes and taxoids are believed to manifest their anticancer effects by promoting polymerization of microtubules (and inhibiting depolymerization) to an extent that is deleterious to cell function, inhibiting cell replication and ultimately leading to cell death.

Figure 6F:
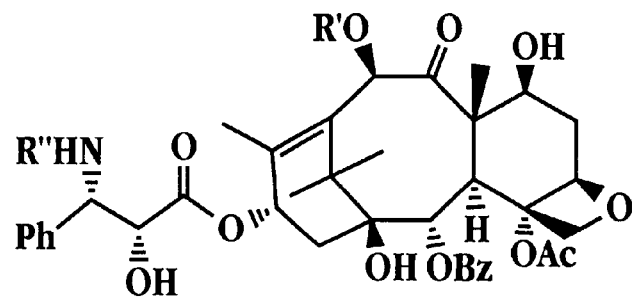
FIGS. 6F and 6G show chemical structures and conventional numbering of constituent backbone atoms for paclitaxel and "TAXOTERE"
Figure 6G:
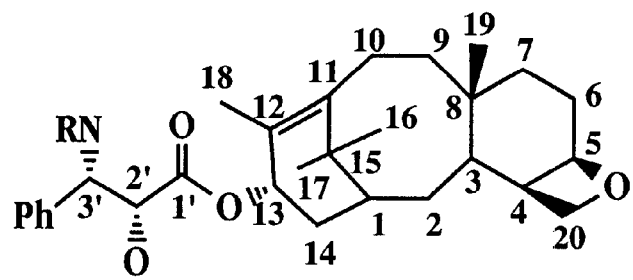
Figure 6H:
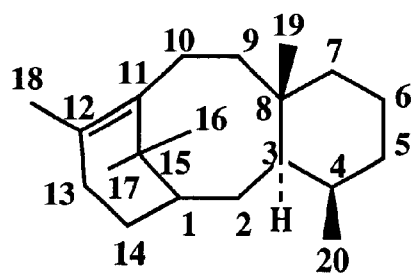
FIG. 6H shows a general chemical structure and ring atom numbering for taxoid compounds.

The term "taxane" refers to paclitaxel (FIG. 6F, R'=acetyl, R"=benzyl) also known under the trademark "TAXOL") and naturally occurring, synthetic, or bioengineered analogs having a backbone core that contains the A, B, C and D rings of paclitaxel, as illustrated in FIG. 6G. FIG. 6F also indicates the structure of "TAXOTERE™" (R'=H, R"=BOC), which is a somewhat more soluble synthetic analog of paclitaxel sold by Rhone-Poulenc. "Taxoid" refers to naturally occurring, synthetic or bioengineered analogs of paclitaxel that contain the basic A, B and C rings of paclitaxel, as shown in FIG. 6H. Substantial synthetic and biological information is available on syntheses and activities of a variety of taxane and taxoid compounds, as reviewed in Suffness (1995), particularly in Chapters 12 to 14, as well as in the subsequent paclitaxel literature. Furthermore, a host of cell lines are available for predicting anticancer activities of these compounds against certain cancer types, as described, for example, in Suffness at Chapters 8 and 13.

The transport polymer is conjugated to the taxane or taxoid moiety via any suitable site of attachment in the taxane or taxoid. Conveniently, the transport polymer is linked via a C2'-oxygen atom, C7-oxygen atom, using linking strategies as above. Conjugation of a transport polymer via a C7-oxygen leads to taxane conjugates that have anticancer and antitumor activity despite conjugation at that position. Accordingly, the linker can be cleavable or non-cleavable. Conjugation via the C2'-oxygen significantly reduces anticancer activity, so that a cleavable linker is preferred for conjugation to this site. Other sites of attachment can also be used, such as C10.

It will be appreciated that the taxane and taxoid conjugates of the invention have improved water solubility relative to taxol (≈0.25 μg/mL) and taxotere (6–7 μg/mL). Therefore, large amounts of solubilizing agents such as "CREMOPHOR EL" (polyoxyethylated castor oil), polysorbate 80 (polyoxyethylene sorbitan monooleate, also known as "TWEEN 80"), and ethanol are not required, so that side-effects typically associated with these solubilizing agents, such as anaphylaxis, dyspnea, hypotension, and flushing, can be reduced.

B. Metals

Metals can be transported into eukaryotic and prokaryotic cells using chelating agents such as texaphyrin or diethylene triamine pentaacetic acid (DTPA), conjugated to a transport membrane of the invention, as illustrated by Example 10. These conjugates are useful for delivering metal ions for imaging or therapy. Exemplary metal ions include Eu, Lu, Pr, Gd, Tc99m, Ga67, In111, Y90, Cu67, and Co57. Preliminary membrane-transport studies with conjugate candidates can be performed using cell-based assays such as described in the Example section below. For example, using europium ions, cellular uptake can be monitored by time-resolved fluorescence measurements. For metal ions that are cytotoxic, uptake can be monitored by cytotoxicity.

C. Macromolecules

The enhanced transport method of the invention is particularly suited for enhancing transport across biological membranes for a number of macromolecules, including, but not limited to proteins, nucleic acids, polysaccharides, and analogs thereof. Exemplary nucleic acids include oligonucleotides and polynucleotides formed of DNA and RNA, and analogs thereof, which have selected sequences designed for hybridization to complementary targets (e.g., antisense sequences for single- or double-stranded targets), or for expressing nucleic acid transcripts or proteins encoded by the sequences. Analogs include charged and preferably uncharged backbone analogs, such as phosphonates (preferably methyl phosphonates), phosphoramidates (N3' or N5'), thiophosphates, uncharged morpholino-based polymers, and protein nucleic acids (PNAs). Such molecules can be used in a variety of therapeutic regimens, including enzyme replacement therapy, gene therapy, and anti-sense therapy, for example.

By way of example, protein nucleic acids (PNA) are analogs of DNA in which the backbone is structurally homomorphous with a deoxyribose backbone. It consists of N-(2-aminoethyl)glycine units to which the nucleobases are attached. PNAs containing all four natural nucleobases hybridize to complementary oligonucleotides obeying Watson-Crick base-pairing rules, and is a true DNA mimic in terms of base pair recognition (Egholm et al., 1993). The backbone of a PNA is formed by peptide bonds rather than phosphate esters, making it well-suited for anti-sense applications. Since the backbone is uncharged, PNA/DNA or PNA/RNA duplexes that form exhibit greater than normal thermal stability. PNAs have the additional advantage that they are not recognized by nucleases or proteases. In addition, PNAs can be synthesized on an automated peptides synthesizer using standard t-Boc chemistry. The PNA is then readily linked to a transport polymer of the invention.

Examples of anti-sense oligonucleotides whose transport into cells may be enhanced using the methods of the invention are described, for example, in U.S. Pat. No. 5,594,122. Such oligonucleotides are targeted to treat human immunodeficiency virus (HIV). Conjugation of a transport polymer to an anti-sense oligonucleotide can be effected, for example, by forming an amide linkage between the peptide and the 5'-terminus of the oligonucleotide through a succinate linker, according to well-established methods. The use of PNA conjugates is further illustrated in Example 11.

Figure 7:
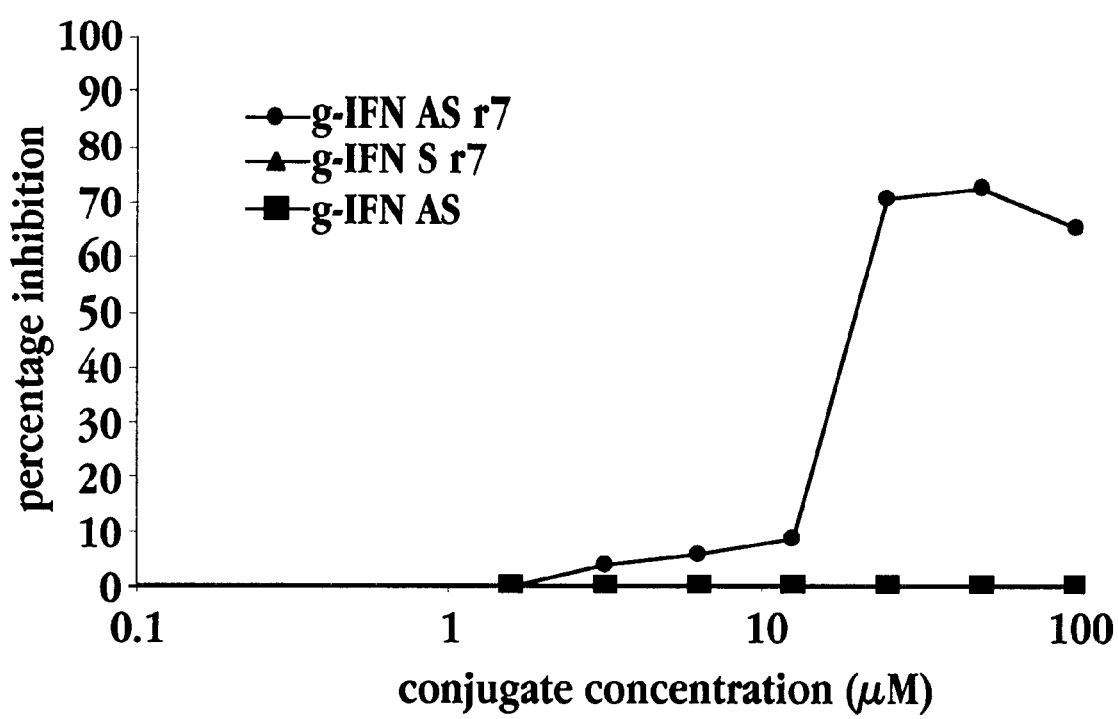
FIG. 7 shows inhibition of secretion of gamma-interferon (γ-IFN) by murine T cells as a function of concentration of a sense-PNA-r7 conjugate (SEQ ID NO:18), antisense PNA-r7 conjugate (SEQ ID NO:19), and non-conjugated antisense PNA (SEQ ID NO:20), where the PNA sequences are based on a sequence from the gene for gamma-interferon.

FIG. 7 shows results obtained with a conjugate of the invention containing a PNA sequence for inhibiting secretion of gamma-interferon (γ-IFN) by T cells, as detailed in Example 11. As can be seen, the anti-sense PNA conjugate was effective to block γ-IFN secretion when the conjugate was present at levels above about 10 $\mu$M. In contrast, no inhibition was seen with the sense-PNA conjugate or the non-conjugated antisense PNA alone.

Another class of macromolecules that can be transported across biological membranes is exemplified by proteins, and in particular, enzymes. Therapeutic proteins include, but are not limited to replacement enzymes. Therapeutic enzymes include, but are not limited to, alglucerase, for use in treating lysozomal glucocerebrosidase deficiency (Gaucher's disease), alpha-L-iduronidase, for use in treating mucopolysaccharidosis I, alpha-N-acetylglucosamidase, for use in treating sanfilippo B syndrome, lipase, for use in treating pancreatic insufficiency, adenosine deaminase, for use in treating severe combined immunodeficiency syndrome, and triose phosphate isomerase, for use in treating neuromuscular dysfunction associated with triose phosphate isomerase deficiency.

In addition, and according to an important aspect of the invention, protein antigens may be delivered to the cytosolic compartment of antigen-presenting cells (APCs), where they are degraded into peptides. The peptides are then transported into the endoplasmic reticulum, where they associate with nascent HLA class I molecules and are displayed on the cell surface. Such "activated" APCs can serve as inducers of class I restricted antigen-specific cytotoxic T-lymphocytes (CTLs), which then proceed to recognize and destroy cells displaying the particular antigen. APCs that are able to carry out this process include, but are not limited to, certain macrophages, B cells and dendritic cells. In one embodiment, the protein antigen is a tumor antigen for eliciting or promoting an immune response against tumor cells.

The transport of isolated or soluble proteins into the cytosol of APC with subsequent activation of CTL is exceptional, since, with few exceptions, injection of isolated or soluble proteins does not result either in activation of APC or induction of CTLs. Thus, antigens that are conjugated to the transport enhancing compositions of the present invention may serve to stimulate a cellular immune response in vitro or in vivo.

Example 14 provides details of experiments carried out in support of the present invention in which an exemplary protein antigen, ovalbumin, was delivered to APCs after conjugation to an R7 polymer. Subsequent addition of the APCs to cytotoxic T lymphocytes (CTLs) resulted in CD8+ albumin-specific cytotoxic T cells (stimulated CTLs). In contrast, APCs that had been exposed to unmodified ovalbumin failed to stimulate the CTLs.

In parallel experiments, histocompatible dendritic cells (a specific type of APC) were exposed to ovalbumin-R7 conjugates, then injected into mice. Subsequent analysis of blood from these mice revealed the presence of albumin-specific CTLs. Control mice were given dendritic cells that had been exposed to unmodified albumin. The control mice did not exhibit the albumin-specific CTL response. These experiments exemplify one of the specific utilities associated with delivery of macromolecules in general, and proteins in particular, into cells.

In another embodiment, the invention is useful for delivering immunospecific antibodies or antibody fragments to the cytosol to interfere with deleterious biological processes such as microbial infection. Recent experiments have shown that intracellular antibodies can be effective antiviral agents in plant and mammalian cells (e.g., Tavladoraki et al., 1993; and Shaheen et al., 1996). These methods have typically used single-chain variable region fragments (scFv), in which the antibody heavy and light chains are synthesized as a single polypeptide. The variable heavy and light chains are usually separated by a flexible linker peptide (e.g., of 15 amino acids) to yield a 28 kDa molecule that retains the high affinity ligand binding site. The principal obstacle to wide application of this technology has been efficiency of uptake into infected cells. But by attaching transport polymers to scFv fragments, the degree of cellular uptake can be increased, allowing the immunospecific fragments to bind and disable important microbial components, such as HIV Rev, HIV reverse transcriptase, and integrase proteins.

D. Peptides

Peptides to be delivered by the enhanced transport methods described herein include, but should not be limited to, effector polypeptides, receptor fragments, and the like. Examples include peptides having phosphorylation sites used by proteins mediating intracellular signals. Examples of such proteins include, but are not limited to, protein kinase C, RAF-1, p21Ras, NF-$_k$B, C-JUN, and cytoplasmic tails of membrane receptors such as IL-4 receptor, CD28, CTLA-4, V7, and MHC Class I and Class II antigens.

When the transport enhancing molecule is also a peptide, synthesis can be achieved either using an automated peptide synthesizer or by recombinant methods in which a polynucleotide encoding a fusion peptide is produced, as mentioned above.

In experiments carried out in support of the present invention (Example 15) a 10-amino acid segment of the cytoplasmic tail region of the transmembrane protein V7 (also known as CD101) was synthesized with an R7 polymer sequence at its C terminus. This tail region is known to physically associate with and mediate the inactivation of RAF-1 kinase, a critical enzyme in the MAP kinase pathway of cellular activation. The V7-R7 conjugate was added to T-cells, which were subsequently lysed with detergent. The soluble fraction was tested for immunoprecipitation by anti-V7 murine antibody in conjunction with goat anti-mouse IgG.

In the absence of peptide treatment, RAF-1, a kinase known to associate with and be inactivated by association with V7, co-precipitated with V7. In peptide treated cells, RAF-1 protein was eliminated from the V7 immuno-complex. The same peptide treatment did not disrupt a complex consisting of RAF-1 and p21 Ras, ruling out any non-specific modification of RAF-1 by the V7 peptides. These results showed that a cytoplasmic tail region V7 peptide, when conjugated to a membrane transport enhancing peptide of the present invention, enters a target cell and specifically associates with a physiological effector molecule, RAF-1. Such association can be used to disrupt intracellular processes.

In a second set of studies, the V7 portion of the conjugate was phosphorylated in vitro using protein kinase C. Anti-RAF-1 precipitates of T cells that had been exposed to the phosphorylated V7 tail peptides, but not the unphosphorylated V7 tail peptide, demonstrated potent inhibition of RAF-kinase activity. These studies demonstrate two principles. First, the transport polymers of the invention can effect transport of a highly charged (phosphorylated) molecule across the cell membrane. Second, while both phosphorylated and unphosphorylated V7 tail peptides can bind to RAF-1, only the phosphorylated peptide modified RAF-1 kinase activity.

VI. Screening Assay Method and Library

In another embodiment, the invention can be used to screen one or more conjugates for a selected biological activity, wherein the conjugate(s) are formed from one or more candidate agents. Conjugate(s) are contacted with a cell that exhibits a detectable signal upon uptake of the conjugate into the cell, such that the magnitude of the signal is indicative of the efficacy of the conjugate with respect to the selected biological activity.

One advantage of this embodiment is that it is particularly useful for testing the activities of agents that by themselves are unable, or poorly able, to enter cells to manifest biological activity. Thus, the invention provides a particularly efficient way of identifying active agents that might not otherwise be accessible through large-scale screening programs, for lack of an effective and convenient way of transporting the agents into the cell or organelle.

Preferably, the one or more candidate agents are provided as a combinatorial library of conjugates which are prepared using any of a number of combinatorial synthetic methods known in the art. For example, Thompson and Ellman (1996) recognized at least five different general approaches for preparing combinatorial libraries on solid supports, namely (1) synthesis of discrete compounds, (2) split synthesis (split and pool), (3) soluble library deconvolution, (4) structural determination by analytical methods, and (5) encoding strategies in which the chemical compositions of active candidates are determined by unique labels, after testing positive for biological activity in the assay. Synthesis of libraries in solution includes at least (1) spatially separate syntheses and (2) synthesis of pools (Thompson, supra). Further description of combinatorial synthetic methods can be found in Lam et al. (1997), which particularly describes the one-bead-one-compound approach.

These approaches are readily adapted to prepare conjugates in accordance with the present invention, including suitable protection schemes as necessary. For example, for a library that is constructed on one or more solid supports, a transport peptide moiety can be attached to the support(s) first, followed by building or appending candidate agents combinatorially onto the polymers via suitable reactive functionalities. In an alternative example, a combinatorial library of agents is first formed on one or more solid supports, followed by appending a transport polymer to each immobilized candidate agent. Similar or different approaches can be used for solution phase syntheses. Libraries formed on a solid support are preferably severed from the support via a cleavable linking group by known methods (Thompson et al., and Lam et al., supra).

The one or more conjugate candidates can be tested with any of a number of cell-based assays that elicit detectable signals in proportion to the efficacy of the conjugate. Conveniently, the candidates are incubated with cells in multiwell plates, and the biological effects are measured via a signal (e.g., fluorescence, reflectance, absorption, or chemiluminescence) that can be quantitated using a plate reader. Alternatively, the incubation mixtures can be removed from the wells for further processing and/or analysis. The structures of active and optionally inactive compounds, if not already known, are then determined, and this information can be used to identify lead compounds and to focus further synthesis and screening efforts.

For example, the γ-interferon secretion assay detailed in Example 11 is readily adapted to a multiwell format, such that active secretion inhibitors can be detected by europium-based fluorescence detection using a plate reader. Anticancer agents can be screened using established cancer cell lines (e.g., provided by the National Institutes of Health (NIH) and the National Cancer Institute (NCI). Cytotoxic effects of anticancer agents can be determined by trypan dye exclusion, for example.

Other examples include assays directed to inhibiting cell signaling, such as IL-4 receptor inhibition; assays for blocking cellular proliferation, and gene expression assays. In a typical gene expression assay, a gene of interest is placed under the control of a suitable promoter and is followed downstream by a gene for producing a reporter species such as β-galactosidase or firefly luciferase. An inhibitory effect can be detected based on a decrease in reporter signal.

The invention also includes a conjugate library which is useful for screening in the above method. The library includes a plurality of candidate agents for one or more selected biological activities, each of which is conjugated to at least one transport polymer in accordance with the invention. Preferably, the conjugate library is a combinatorial library. In another embodiment, the invention includes a regular array of distinct polymer-agent conjugates distributed in an indexed or indexable plurality of sample wells, for testing and identifying active agents of interest.

VI. Utility

Compositions and methods of the present invention have particular utility in the area of human and veterinary therapeutics. Generally, administered dosages will be effective to deliver picomolar to micromolar concentrations of the therapeutic composition to the effector site. Appropriate dosages and concentrations will depend on factors such as the therapeutic composition or drug, the site of intended delivery, and the route of administration, all of which can be derived empirically according to methods well known in the art. Further guidance can be obtained from studies using experimental animal models for evaluating dosage, as are known in the art.

Administration of the compounds of the invention with a suitable pharmaceutical excipient as necessary can be carried out via any of the accepted modes of administration. Thus, administration can be, for example, intravenous, topical, subcutaneous, transcutaneous, intramuscular, oral, intra-joint, parenteral, peritoneal, intranasal, or by inhalation. The formulations may take the form of solid, semisolid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art, e.g., (Gennaro, 1990).

For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see *Remington's Pharmaceutical Sciences* (1980). The composition to be administered will, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

Stability of the conjugate can be further controlled by the composition and stereochemistry of the backbone and sidechains of the polymer. For polypeptide polymers, D-isomers are generally resistant to endogenous proteases, and therefore have longer half-lives in serum and within cells. D-polypeptide polymers are therefore appropriate when longer duration of action is desired. L-polypeptide polymers have shorter half-lives due to their susceptibility to proteases, and are therefore chosen to impart shorter acting effects. This allows side-effects to be averted more readily by withdrawing therapy as soon as side-effects are observed. Polypeptides comprising mixtures of D and L-residues have intermediate stabilities. Homo-D-polymers are generally preferred.

The following examples are intended to illustrate but not limit the present invention.

EXAMPLE 1

Peptide Synthesis

Peptides were synthesized using solid phase techniques on an Applied Biosystems Peptide synthesizer using Fast-MOC™ chemistry and commercially available Wang resins and Fmoc protected amino acids, according to methods well known in the art (Bonifaci). Peptides were purified using C4 or C18 reverse phase HPLC columns, and their structures were confirmed using amino acid analysis and mass spectrometry.

EXAMPLE 2

Fluorescence Assays

Fluorescent peptides were synthesized by modification of the amino terminus of the peptide with aminocaproic acid followed by reaction with fluorescein isothiocyanate in the presence of (2-1H-benzotriazol-1-yl)-1,1,3,3-tetramethyl uronium hexafluorophosphate/N-hydroxy benzotriazole dissolved in N-methyl pyrrolidone. The products were purified by gel filtration.

Suspension cells (106/mL) were incubated for varying times, at 37° C., 23° C., or 4° C., with a range of concentrations of peptides or conjugates in PBS pH 7.2 containing 2% fetal calf serum (PBS/FCS) in 96 well plates. After a minute incubation, the cells were pelleted by centrifugation, washed three times with PBS/FCS containing 1% sodium azide, incubated with trypsin/EDTA (Gibco) at 37° C. for five minutes, then washed twice more with PBS/FCS/NaN$_3$. The pelleted cells were resuspended in PBS containing 2% FCS and 0.1% propidium iodide and analyzed on a FACS-can (Becton Dickenson, Mountain View, Calif.). Cells positive for propidium iodide were excluded from the analysis. For analysis of polymers of arginine, the voltage of the photomultiplier was reduced by an order of magnitude to allow a more accurate measurement.

EXAMPLE 3

Tat Basic Peptide Versus Poly-Arg Peptides

Uptake levels of the following polypeptides were measured by the method in Example 2: (1) a polypeptide comprising HIV tat residues 49–57 (Arg-Lys-Lys-Arg-Arg-Gln-Arg-Arg-Arg=SEQ ID NO:1), (2) a nonamer of L-Lys residues (K9, SEQ ID NO:2), and (3) homo-L or homo-polypeptides containing four to nine Arg residues (SEQ ID NO:3–8 and 12–17). Results are shown in FIGS. 2A–2C.

EXAMPLE 4

Confocal Cell Microscopy

Cells incubated with fluorescent polyarginine peptides were prepared as described above for binding assays and analyzed at the Cell Sciences Imaging Facility (Stanford University, Stanford, Calif.) using a scanning, single beam laser confocal microscope, with an excitation wavelength of 488 nm (argon-ion laser) and an emission band-width of 510–550 using a band-pass filter. Conjugates (6.25 µM) containing tat(49–57), R7, or r7 coupled to fluorescein were incubated with Jurkat cells for 37° C. for 10 minutes. FIGS. 2A–2F show results for emitted fluorescence (FIGS. 2A–2C) and transmitted light (2D—2F) for tat(49–57) (FIGS. 2A and 2C), R7 (FIGS. 2B and 2E), and r7 (FIGS. 2C and 2F).

EXAMPLE 5

Length Range Studies

The following homopolymers of polyarginine were tested by the fluorescence assay in Example 2, with incubation at 37° C. for 15 minutes prior to cell pelleting: r9, R9, R15, R20, R25, and R30. In addition, a mixture of L-arginine polymers having an average molecular weight of 12,000 daltons (approximately 100 amino acids) was also tested (Sigma Chem. Co.) after being labeled with fluorescein isothiocyanate and purified by gel filtration ("SEPHADEX" G-25). The cells were analyzed by FACS, and the mean fluorescence of the live cells was measured. Cytotoxicity of each conjugate was also measured by calculating the percentage of cells that stained with propidium iodide, which is characteristic of cell death. Uptake results for the r9, R9, R15, R20, and R25 conjugates are shown in FIG. 3.

The commercially available polyarginine (12,000 MW) precipitated proteins in serum, most likely α1-acid glycoprotein. Therefore, the level of fetal calf serum was reduced 10-fold in the assay for conjugates prepared from this material.

The 12,000 MW poly-Arg composition was toxic at concentrations from 800 nM to 50 µM and is excluded from FIG. 3. Poly-L-Arg conjugates containing 20 arginine residues or more were toxic at concentrations greater than 12 µM, such that toxicity increased with length.

EXAMPLE 6

Kinetics of Uptake

To measure Vmax and Km parameters of cellular uptake, the assay method of Example 2 was used with the following modifications. Peptides were incubated with cells for 0.5, 1, 2, and 4 minutes at 4° C. in triplicate, in 50 µL of PBS/FCS in 96-well plates. At the end of incubation, the reaction was quenched by diluting the samples in 5 mL of PBS/FCS, centrifuging and washing once with PBS/FCS, trypsin/EDTA, and finally again with PBS/FCS, and taking up the pellets in PBS/FCS containing propidium iodide for analysis on a FACScan. FACS data were fitted to the Line-weaver-Burk equation for Michaelis-Menten kinetics.

Kinetic data for fluorescent conjugates of tat(49–57), R9, and r9 are shown in Table 1 above.

EXAMPLE 7

Metabolic Inhibitor Effects on Transport

Suspension cells ($10^6$/mL) were incubated for 30 minutes with 0.5% sodium azide in PBS containing 2% FCS. At the end of incubation, fluorescent peptides (tat(49–57)), R7, R8, or R9) were added to a final concentration of 12.5 µM. After incubation for 30 minutes, the cells were washed as in Example 2, except that all wash buffers contained 0.1% sodium azide. The results are shown in FIG. 5.

EXAMPLE 8

Transport into Bacterial Cells

Gram-negative bacteria (*E. coli* strain HB101) and gram-positive bacteria (*Strep. bovis*) were grown in appropriate media in logarithmic phase. Cell cultures ($4 \times 10^8$ per mL) were incubated for 30 minutes at 37° C. with varying concentrations of fluorescent conjugates containing linear polymers of L-arginine (R4 through R9), D-arginine (r4 through r9), or L-lysine (K9) at conjugate concentrations of 3 to 50 µM. The cells were washed and taken up in PBS-containing propidium iodide (to distinguish dead cells) and analyzed by FACS and fluorescent microscopy. Results are shown in FIGS. 5A–5C as discussed above.

EXAMPLE 9

Conjugates with Exemplary Cleavable Linkers

A. 6-Mercaptopurine Cysteine Disulfide Conjugate

A1. Thiol Activation. N-acetyl-Cys(SH)-Ala-Ala-Ala-(Arg)$_7$—CO$_2$H (12.2 mg, 0.0083 mmol) (SEQ ID NO: 20) was dissolved in 3 mL of 3:1 AcOH:H$_2$O with stirring at ambient temperature. To this solution was added dithio-bis (5-nitropyridine) (DTNP) (12.9 mg, 0.0415 mmol, 5 eq). The solution was permitted to stir for 24 h at ambient temperature, after which the mixture took on a bright yellow color. Solvent was removed in vacuo, and the residue was redissolved in 5 mL of H$_2$O and extracted 3 times with ethyl acetate to remove excess DTNP. The aqueous layer was lyophilized, and the product was used without further purification.

A2. Attachment of Drug N-acetyl-Cys(SH)-Ala-Ala-Ala-(Arg)$_7$—CO$_2$H (0.0083 mmol) (SEQ ID NO: 20) was dissolved in 1 mL of degassed H$_2$O (pH=5) under argon at room temperature, with stirring. 6-Mercaptopurine (1.42 mg, 0.0083 mmol, 1 eq) in 0.5 mL DMF was added to the mixture. The reaction was permitted to stir for 18 h under inert atmosphere at ambient temperature. After 18 h, a bright yellow color developed, indicating the presence of free 5-nitro-2-thiopyridine. Solvent was removed under reduced pressure, and the residue was purified by HPLC, providing the desired product (I, FIG. 6A) in 50% overall yield.

B. Photocleavable Taxol Conjugate

3-Nitro-4-(bromomethyl)benzoic acid (100 mg, 0.384 mmol) is dissolved in anhydrous methanol (5 mL) under an atmosphere of nitrogen. To this solution is added sodium methoxide (88 µL, 25% (w/w) in methanol, 0.384 mmol, 1 eq) followed by addition of 6-mercaptopurine (58.2 mg, 0.384 mmol, 1 eq). The mixture is warmed to reflux and permitted to stir for 3 h. The reaction mixture is then cooled, filtered, and quenched by acidification with 6N HCl. The reaction volume is then reduced to one-half at which point the product precipitates and is collected by filtration. The residue is redissolved in methanol, filtered (if necessary) and concentrated under reduced pressure to provide desired sulfide (II, FIG. 6B) in 50% yield as a yellow powdery solid.

C. Phosphate-Cleavable Taxol Conjugate

C1. To a suspension of o-hydroxy phenylacetic acid (15.0 g, 0.099 mol) in $H_2O$ (39 mL) at 0° C. was added a solution of nitric acid (12 mL of 65% in 8 mL $H_2O$) slowly via pipette. The solution was stirred for an additional 1.5 h at 0° C. The mixture was then warmed to ambient temperature and allowed to stir for an additional 0.5 h. The heterogeneous solution was poured over ice (10 g) and filtered to remove the insoluble ortho-nitro isomer. The reddish solution was concentrated under reduced pressure, and the thick residue was redissolved in 6N HCl and filtered through celite. The solvent was again removed under reduced pressure to provide the desired 2-hydroxy-4-nitro-phenylacetic acid as a light, brownish-red solid (40% yield). The product (IV-a) was used in the next step without further purification.

C2. Product IV-a (765 mg, 3.88 mmol) was dissolved in freshly distilled THF (5 mL) under argon atmosphere. The solution was cooled to 0° C., and borane-THF (1.0 M in THF, 9.7 mL, 9.7 mmol, 2.5 eq) was added dropwise via syringe with apparent evolution of hydrogen. The reaction was permitted to stir for an additional 16 h, slowly warming to room temperature. The reaction was quenched by slow addition of 1M HCl (with furious bubbling) and 10 mL of ethyl acetate. The layers were separated and the aqueous layer extracted five times with ethyl acetate. The combined organic layers were washed with brine and dried over magnesium sulfate. The solvent was evaporated in vacuo and the residue purified by rapid column chromatography (1:1 hexane:ethyl acetate) to provide the desired nitro-alcohol (IV-b) as a light yellow solid (85% yield).

C3. Nitro-alcohol (IV-b) (150 mg, 0.819 mmol) was dissolved in dry DMF (5 mL) containing di-t-butyldicarbonate (190 mg, 1.05 eq) and 10% Pd-C (10 mg). The mixture was placed in a Parr apparatus and pressurized/purged five times. The solution was then pressurized to 47 psi and allowed to shake for 24 h. The reaction was quenched by filtration through celite, and the solvent was removed under reduced pressure. The residue was purified by column chromatography (1:1 hexane:ethyl acetate) to provide the protected aniline product (IV-c) as a tan crystalline solid in 70% yield.

C4. TBDMS-Cl (48 mg, 0.316 mmol) was dissolved in freshly distilled dichloromethane (4 mL) under an argon atmosphere. To this solution was added imidazole (24 mg, 0.347 mmol, 1.1 eq) and immediately a white precipitate formed. The solution was stirred for 30 min at room temperature, at which point product IV-c (80 mg, 0.316 mmol, 1.0 eq) was added rapidly as a solution in dichloromethane/THF (1.0 mL). The resulting mixture was permitted to stir for an additional 18 h at ambient temperature. Reaction was quenched by addition of saturated aqueous ammonium chloride. The layers were separated and the aqueous phase extracted 3 times with ethyl acetate and the combined organic layers washed with brine and dried over sodium sulfate. The organic phase was concentrated to provide silyl ether-phenol product (IV-d) as a light yellow oil (90% yield).

C5. Silyl ether-phenol IV-d (150 mg, 0.408 mmol) was dissolved in freshly distilled THF (7 mL) under argon and the solution cooled to 0C. n-BuLi (2.3 M in hexane, 214 uL) was then added dropwise via syringe. A color change from light yellow to deep red was noticed immediately. After 5 min, tetrabenzyl pyrophosphate (242 mg, 0.45 mmol, 1.1 eq) was added rapidly to the stirring solution under argon. The solution was stirred for an additional 18 h under inert atmosphere, slowly warming to room temperature, during which time a white precipitate forms. The reaction was quenched by addition of saturated aqueous ammonium chloride and 10 mL of ethyl acetate. The layers were separated, and the aqueous layer was extracted 5 times with ethyl acetate. The combined organic phases were washed with brine and dried over magnesium sulfate. The solvent was removed by evaporation and the residue purified by rapid column chromatography (1:1 hexane:ethyl acetate) to provide the desired phosphate-silyl ether (IV-e) as a light orange oil (90% yield).

C6. Phosphate-silyl ether (IV-e) (10 mg, 0.0159 mmol) was dissolved in 2 mL of dry ethanol at room temperature. To the stirring solution was added 20 uL of conc. HCl (1% v:v solution), and the mixture was permitted to stir until TLC analysis indicated the reaction was complete. Solid potassium carbonate was added to quench the reaction, and the mixture was rapidly filtered through silica gel and concentrated to give crude alcohol-dibenzyl phosphate product (IV-f) as a light yellow oil (100% yield).

C7. Alcohol IV-f (78 mg, 0.152 mmol) was dissolved in freshly distilled dichloromethane (10 mL) under an argon atmosphere. To the solution was added Dess-Martin is periodinane (90 mg, 0.213 mmol, 1.4 eq). The solution was permitted to stir, and the progress of the reaction was monitored by TLC analysis. Once TLC indicated completion, reaction was quenched by addition of 1:1 saturated aqueous sodium bicarbonate:saturated aqueous sodium thiosulfite. The biphasic mixture was permitted to stir for 1 h at ambient temperature. The layers were separated, and the aqueous phase was extracted 3 times with ethyl acetate. The combined organic layers were washed with brine and dried over sodium sulfate. Solvent was removed under reduced pressure to provide aldehyde product (IV-g) as a light tan oil (100% yield).

C8. Aldehyde IV-g (78 mg, 0.152 mmol) was dissolved in t-butanol/water (3.5 mL) under inert atmosphere. To the rapidly stirring solution was added 2-methyl-2-butene (1.0 M in THF, 1.5 mL), sodium phosphate-monobasic (105 mg, 0.76 mmol, 5 eq) and sodium chlorite (69 mg, 0.76 mmol, 5 eq). The solution was permitted to stir for 8 additional hours at room temperature. The solution was concentrated, and the residue was acidified and extracted with ethyl acetate 3 times. The combined organic phases were dried over magnesium sulfate. The solution was again concentrated under reduced pressure and the residue was purified via column chromatography (2:1 ethyl acetate:hexane) to give the desired carboxylic acid-dibenzylphosphate (IV-h) as a light yellow oil (65% yield).

C9. Acid IV-h (8.0 mg, 0.0152 mmol, 1.1 eq) was dissolved in freshly distilled dichloromethane (2 mL) under argon at ambient temperature. To this mixture was added paclitaxel (12 mg, 0.0138 mmol, 1 eq) followed by DMAP (2 mg, 0.0138 mmol, 1 eq) and DCC (3.2 mg, 0.0152, 1.1 eq). The mixture was allowed to stir at room temperature for an additional 4 h, during which a light precipitate formed. Once TLC analysis indicated that the reaction was complete, solvent was removed under reduced pressure, and the residue was purified by rapid column chromatography (1:1 hexane:ethyl acetate) to provide paclitaxel-C2'-carboxylate ester (IV-i) as a white, crystalline solid (65% yield).

C10. Ester IV-i (5.0 mg) was dissolved in neat formic acid (1.0 mL) under an argon atmosphere at room temperature and permitted to stir for 30 min. Once TLC indicated that the reaction was complete, the solution was concentrated under reduced pressure and the residue purified by rapid filtration through silica gel to give the desired aniline-taxol compound (IV-j) in 50% yield as a white powder.

C11. To a solution of (poly di-CBZ)-protected AcHN-RRRRRRR-CO$_2$H (1.2 eq, 0.1 to 1.0 M) (SEQ ID NO: 6) in dry DMF was added O-benzotriazolyloxy tetramethyluronium hexafluorophosphate (HATU, 1.0 eq) and a catalytic amount of DMAP (0.2 eq). The solution stirred under inert atmosphere for 5 min at ambient temperature. To this mixture was then added Taxol-aniline derivative (IV-j) as a solution in dry DMF (minimal volume to dissolve). The resulting solution was stirred for an additional 5 h at room temperature. Reaction was terminated by concentrating the reaction mixture under reduced pressure. The crude reaction mixture was then purified by HPLC to provide the desired material (IV, FIG. 6D).

EXAMPLE 10

Transport of Metal Ions 3.93 g of DTPA is dissolved in 100 mls of HEPES buffer and 1.52 ml of europium chloride atomic standard solution (Aldrich) dissolved in 8 ml of HEPES buffer is added and stirred for 30 minutes at room temperature.

Chromatographic separation and lyophilization affords an Eu-DTPA chelate complex. This complex is then conjugated to the amino terminus of a polypeptide by solid phase peptide chemistry. The cellular uptake of europium ion can be monitored by time resolved fluorescence.

EXAMPLE 11

Uptake of PNA-Peptide Conjugates

PNA peptide conjugates were synthesized using solid phase chemistry with commercially available Fmoc reagents (PerSeptive Biosystems, Cambridge, Mass.) on either an Applied Biosystems 433A peptide synthesizer or a Millipore Expedite nucleic acid synthesis system. Polymers of D or L-arginine were attached to the amino or carboxyl termini of the PNAs, which are analogous to the 5' and 3' ends of the nucleic acids, respectively. The conjugates were also modified to include fluorescein or biotin by adding an aminocaproic acid spacer to the amino terminus of the conjugate and then attaching biotin or fluorescein. The PNA-peptide conjugates were cleaved from the solid phase resin using 95% TFA, 2.5% triisopropyl silane, and 2.5% aqueous phenol. The resin was removed by filtration, and residual acid was removed by evaporation. The product was purified by HPLC using a C-18 reverse phase column, and the product was lyophilized. The desired PNA-polymer conjugates were identified using laser desorption mass spectrometry.

A. Inhibition of Cellular Secretion of Gamma-IFN

1. PNA-Peptide Conjugates. The following sense and antisense PNA-peptide conjugates were prepared for inhibiting gamma-IFN production, where r=D-arginine, and R=L-arginine:

Sense:
NH$_2$-rrrrrrr-AACGCTACAC-COOH (SEQ ID NO:18)
Antisense:
NH$_2$-rrrrrrr-GTGTAGCGTT-COOH (SEQ ID NO:19)
Fluorescent antisense:
X-rrrrrrr-GTGTAGCGTT-COOH (X-SEQ ID NO:19)
where X=fluorescein-aminocaproate
Biotinylated antisense:
Z-rrrrrrr-GTGTAGCGTT-COOH (Z-SEQ ID NO:19)
where Z=biotin-aminocaproate 2. Uptake by T Cells. To show that PNA-polyarginine conjugates enter cells effectively, the fluorescent antisense conjugate above (X-SEQ ID NO:19) was synthesized by conjugating fluorescein isothiocyanate to the amino terminus of SEQ ID NO:18 using an aminocaproic acid spacer.

Cellular uptake was assayed by incubating the Jurkat human T cell line ($5 \times 10^5$ cells/well) either pretreated for minutes with 0.5% sodium azide or phosphate buffered saline, with varying amounts (100 nM to 50 μM) of the fluorescein-labeled sense and antisense PNA-r7 conjugate, as well as the antisense PNA alone (without r7 segment). The amount of antisense PNA that entered the cells was analyzed by confocal microscopy and FACS. In both cases, fluorescent signals were present only in cells not exposed to azide, and the fluorescent signal was dependent on the dose of the fluorescent conjugate and on the temperature and duration of incubation.

3. Gamma-IFN Assay. The amount of gamma interferon secreted by a murine T cell line (clone 11.3) was measured by incubating $10^5$ T cells with varying amounts of antigen (peptide consisting of residues 110–121 of sperm whale myoglobin) and histocompatible spleen cells from DBA/2 mice (H-2d, $5 \times 10^5$), which act as antigen-presenting cells (APCs), in 96 well plates. After incubation for 24 hours at 37° C., 100 μL of the supernatants were transferred to microtiter plates coated with commercially available anti-gamma-IFN monoclonal antibodies (Mab) (Pharmingen, San Diego, Calif.). After incubation for an hour at room temperature, the plates were washed with PBS containing 1% fetal calf serum and 0.1% Tween®20, after which a second, biotinylated gamma-IFN Mab was added. After a second hour of incubation, the plates were washed as before, and europium (Eu)-streptavidin (Delphia-Pharmacia) was added. Again, after an hour of incubation, an acidic buffer was added to release Eu, which was measured by time-resolved fluorometry on a Delphia plate reader. The amount of fluorescence was proportional to the amount of gamma-IFN that had been produced and could be quantified precisely using known amounts of gamma-IFN to create a standard curve.

4. Inhibition of Gamma-IFN Production by Conjugates.

The ability of PNA-polyarginine conjugates to inhibit secretion of gamma-IFN was assayed by adding various concentrations of the above gamma-IFN conjugates with suboptimal doses of peptide antigen (0.5 μM), to a mixture of clone 11.3 T cells and histocompatible spleen cells. PNA sequences lacking polyarginine moieties, and non-conjugated D-arginine heptamer, were also tested.

After 24 hours, aliquots of the cultured supernatants were taken, and the amount of gamma-IFN was measured using the fluorescent binding assay described in section 3 above. Treatment of cells with the antisense PNA-r7 conjugate resulted in an over 70% reduction in IFN secretion, whereas equivalent molar amounts of the sense PNA-r7, antisense PNA lacking r7, or r7 alone all showed no inhibition (FIG. 7).

EXAMPLE 12

Transport of Large Protein Antigen Into APCs

A conjugate of ovalbumin coupled to a poly-L-arginine heptamer was formed by reacting a cysteine-containing polypeptide polymer (Cys-Ala-Ala-Ala-Arg$_7$, SEQ ID NO: 20) with ovalbumin (45 kDa) in the presence of sulfo-MBS, a heterobifunctional crosslinker (Pierce Chemical Co., Rockford, Ill.). The molar ratio of peptide conjugated to ovalbumin was quantified by amino acid analysis. The conjugate product was designated OV-R7. The conjugate was added (final concentration 10 μM) to B-cells, also referred to as antigen-presenting cells (APCs), which were isolated according to standard methods. The APCs were incubated with OV-R7, and then were added to a preparation of cytotoxic T-lymphocytes isolated by standard methods. Exposure of CTLs to APCs that had been incubated with OV-R7 produced CD8+ albumin-specific CTLs. In contrast, APCs that had been exposed to unmodified ovalbumin failed to stimulate the CTLs.

In another experiment, histocompatible dendritic cells (a specific type of APC) were exposed to albumin-R7 conjugates and were then injected into mice. Subsequent analysis of blood from these mice revealed the presence of albumin-specific CTLs. Control mice were given dendritic cells that had been exposed to unmodified albumin. The control mice did not exhibit the albumin-specific CTL response.

EXAMPLE 13

Enhanced Uptake of V7-Derived Peptide

A on conjugate consisting of a portion of the C-terminal cytoplasmic tail region of V7 (a leukocyte surface protein) having the sequence KLSTLRSNT (SEQ ID NO: 21; Ruegg et al., 1995) was synthesized with 7 arginine residues attached to its C-terminus according to standard methods using a peptide synthesizer (Applied Biosystems Model 433). The conjugate was added (final concentration ≈10 μM) to T-cells which had been isolated by standard methods, and was incubated at 37° C. for several hours to overnight. Cells were lysed using detergent (1% Triton X-100). DNA was removed, and the soluble (protein-containing) fraction was subjected to immunoprecipitation with an anti-V7 murine monoclonal antibody in combination with goat anti-mouse IgG. RAF-1 is a kinase that associates with, and is inactivated by association with, V7.

In the absence of peptide treatment, RAF-1 protein co-precipitated with V7. In peptide-treated cells, RAF-1 protein was eliminated from the V7 immunocomplex. The same peptides were unable to disrupt a complex consisting of RAF-1 and p21 Ras, ruling out non-specific modification of RAF-1 by the V7 peptide.

In a second study, the V7 peptide portion of the V7-poly-arginine conjugate was phosphorylated in vitro using protein kinase C. Anti-RAF-1 precipitates of T cells that had been exposed to the phosphorylated V7 tail peptides, but not the unphosphorylated V7 tail peptide, demonstrated potent inhibition of RAF-kinase activity.

While the invention has been described with reference to specific methods and embodiments, it will be appreciated that various modifications and changes may be made without departing from the spirit of the invention.

---

What is claimed is:

1. A conjugate for administration, to a mammalian subject, of an antimicrobial agent whose efficacy in non-conjugated form is limited by its solubility in aqueous liquid or its inability to cross biological membranes to manifest biological activity, said conjugate comprises a transport peptide covalently attached by a linker to the antimicrobial agent, said linker being cleaved in vivo to release the antimicrobial agent from the linker and the transport peptide, wherein the attached transport peptide:

(a) consists of from 6 to 25 amino acid residues, at least 50% of which contain a guanidino sidechain having the structure

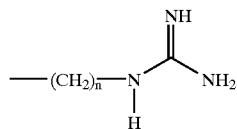

or an amidino sidechain having the structure

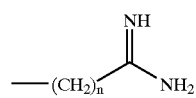

wherein n is 2, 3, 4 or 5;

(b) contains at least 6 contiguous amino acid residues containing said guanidino or amidino sidechain; and (c) increases the delivery of the antimicrobial agent across a biological membrane relative to the delivery of the antimicrobial agent in non-conjugated form.

2. The conjugate of claim 1, wherein at least 70% of the amino acid residues in the transport peptide contain said guanidino sidechain.

3. The conjugate of claim 1, wherein the transport peptide consists of from 7 to 20 amino acid residues.

4. The conjugate of claim 1, wherein each amino acid residue contains said guanidino sidechain.

5. The conjugate of claim 1, wherein all of the amino acid residues are arginine residues.

6. The conjugate of claim 5, wherein at least one of the arginine residues has a D-configuration.

7. The conjugate of claim 6, wherein all of the arginine residues have a D-configuration.

8. The conjugate of claim 1, wherein the transport peptide is attached at least one terminus to a flanking moiety that does not significantly affect the delivery of the antimicrobial agent across biological membranes.

9. The conjugate of claim 8, wherein the transport peptide has a first terminus and a second terminus, with the first terminus attached to a first flanking moiety and the second terminus conjugated to the antimicrobial agent through the linker.

10. The conjugate of claim 9, wherein a second flanking moiety is attached to the second terminus, such that the linker is attached to the second flanking moiety.

11. The conjugate of claim 9, where the first flanking moiety comprises one or more amino acid residues that do not contain said guanidino sidechain or said amidino sidechain.

12. The conjugate of claim 10, where the first flanking moiety and the second flanking moiety comprise one or more amino acid residues that do not contain said guanidino sidechain or said amidino sidechain.

13. The conjugate of claim 9, wherein the first flanking moiety is a blocking group effective to prevent ubiquitination in vivo.

14. The conjugate of claim 13, wherein the blocking group is an acetyl or benzyl group.

15. The conjugate of claim 1, wherein the linker contains a linkage that is chemically, enzymatically or photolytically cleaved in vivo.

16. The conjugate of claim 15, wherein the linkage is a carbamate, ester, thioether, disulfide or hydrazone linkage.

17. The conjugate of claim 1, wherein n is 3.

18. A pharmaceutical composition for administration, to a human subject, of an antimicrobial agent whose efficacy in non-conjugated form is limited by its aqueous solubility, said composition comprising the conjugate of claim 1 and a pharmaceutically acceptable carrier.

* * * * *